(12) United States Patent
Ahmad et al.

(10) Patent No.: US 9,702,886 B2
(45) Date of Patent: Jul. 11, 2017

(54) METHODS AND DEVICES FOR TUBERCULOSIS DIAGNOSIS USING BIOMARKER PROFILES

(71) Applicants: The Broad Institute, Inc., Cambridge, MA (US); The General Hospital Corporation, Boston, MA (US)

(72) Inventors: Rushdy Ahmad, Sharon, MA (US); Michael Gillette, Belmont, MA (US); Steven A. Carr, Boxford, MA (US)

(73) Assignees: The Broad Institute, Inc., Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/402,727

(22) PCT Filed: May 24, 2013

(86) PCT No.: PCT/US2013/042620
§ 371 (c)(1),
(2) Date: Nov. 21, 2014

(87) PCT Pub. No.: WO2013/177502
PCT Pub. Date: Nov. 28, 2013

(65) Prior Publication Data
US 2015/0148247 A1 May 28, 2015

Related U.S. Application Data

(60) Provisional application No. 61/651,510, filed on May 24, 2012, provisional application No. 61/780,121, filed on Mar. 13, 2013.

(51) Int. Cl.
| *A61K 39/04* | (2006.01) |
| *A61K 39/00* | (2006.01) |
| *G01N 33/53* | (2006.01) |
| *G01N 33/68* | (2006.01) |
| *G01N 33/569* | (2006.01) |
| *G01N 33/74* | (2006.01) |

(52) U.S. Cl.
CPC ..... *G01N 33/6893* (2013.01); *G01N 33/5695* (2013.01); *G01N 33/6869* (2013.01); *G01N 33/74* (2013.01); *A61K 39/04* (2013.01); *G01N 2333/475* (2013.01); *G01N 2333/54* (2013.01); *G01N 2333/5412* (2013.01); *G01N 2333/5421* (2013.01); *G01N 2333/7155* (2013.01); *G01N 2800/26* (2013.01)

(58) Field of Classification Search
CPC ...... C07K 16/00; C07K 14/195; G01N 33/50; G01N 33/53; G01N 2800/00
USPC ......... 424/130.1, 164.1, 184.1, 248.1; 435/4, 435/7.1, 7.2
See application file for complete search history.

(56) References Cited

U.S. PATENT DOCUMENTS

| 7,323,143 B2 | 1/2008 | Anderson et al. |
| 7,897,356 B2 | 3/2011 | Klass et al. |
| 2002/0051971 A1 | 5/2002 | Stuelpnagel et al. |
| 2008/0267999 A1 | 10/2008 | Tainsky et al. |

FOREIGN PATENT DOCUMENTS

| WO | WO 2006/125973 A2 | 11/2006 |
| WO | WO 2013/177502 A1 | 11/2013 |

OTHER PUBLICATIONS

International Search Report and Written Opinion for Application No. PCT/US2013/042620 mailed Sep. 12, 2013.
International Preliminary Report on Patentability for Application No. PCT/US2013/042620 mailed Dec. 4, 2014.
[No Author Listed], Human Inflammation MAP® v1.0. Myriad RBM. http://rbm.myriad.com/products-services/humanmap-services/human-inflammationmap/ [last accessed Feb. 5, 2015]. 3 pages.
Conradie et al., Natural killer cell activation distinguishes *Mycobacterium tuberculosis*-mediated immune reconstitution syndrome from chronic HIV and HIV/MTB coinfection. J Acquir Immune Defic Syndr. Nov. 1, 2011;58(3):309-18. doi: 10.1097/QAI.0b013e31822e0d15. Epub Nov. 1, 2011. 18 pages.
Griffin et al., Aetiology, pathogenesis and diagnosis of *Mycobacterium bovis* in deer. Vet Microbiol. May 1994;40(1-2):193-205. Review.
Hrabec et al., Circulation level of matrix metalloproteinase-9 is correlated with disease severity in tuberculosis patients. Int J Tuberc Lung Dis. Aug. 2002;6(8):713-9.
Lai et al., Circulating adhesion molecules in tuberculosis. Clin Exp Immunol. Dec. 1993;94(3):522-6.
Martinez et al., Three-dimensional microfluidic devices fabricated in layered paper and tape. Proc Natl Acad Sci U S A. Dec. 16, 2008;105(50):19606-11. doi: 10.1073/pnas.0810903105. Epub Dec. 8, 2008.
Rahman, Mucosal immunity against mycobacterial infection. Thesis. Stockholm University. 2010;4,54-5.
Rusling et al., Measurement of biomarker proteins for point-of-care early detection and monitoring of cancer. Analyst. Oct. 2010;135(10):2496-511. doi: 10.1039/c0an00204f. Epub Dec. 6, 2010. 31 pages.

*Primary Examiner* — Rodney P Swartz
(74) *Attorney, Agent, or Firm* — Wolf, Greenfield & Sacks, P.C.

(57) ABSTRACT

The invention relates to tuberculosis diagnostic methods and devices that measure particular biomarker profiles in subjects and identify a subject having tuberculosis based on such profiles.

21 Claims, 25 Drawing Sheets

| Row | Rank | Upregulated In | Feature | Description | Score | Feature P | Feature P Low | Feature P High | FDR(BH) | Q Value | Bonferroni |
|---|---|---|---|---|---|---|---|---|---|---|---|
| 1 | 1 | TB | IL6 | IL6 | -6.532 | 0.002 | 0 | 0.003 | 0.005 | 0.007 | 0.068 |
| 2 | 2 | TB | AAT | AAT | -6.413 | 0.002 | 0 | 0.003 | 0.005 | 0.007 | 0.068 |
| 3 | 3 | TB | CRP | CRP | -6.217 | 0.002 | 0 | 0.003 | 0.005 | 0.007 | 0.068 |
| 4 | 4 | TB | IL8 | IL8 | -5.815 | 0.002 | 0 | 0.003 | 0.005 | 0.007 | 0.068 |
| 5 | 5 | TB | VEGF | VEGF | -5.754 | 0.002 | 0 | 0.003 | 0.005 | 0.007 | 0.068 |
| 6 | 6 | TB | Haptoglobin | Haptoglobin | -5.07 | 0.002 | 0 | 0.003 | 0.005 | 0.007 | 0.068 |
| 7 | 7 | TB | TNFR2 | TNFR2 | -4.396 | 0.002 | 0 | 0.003 | 0.005 | 0.007 | 0.068 |
| 8 | 8 | TB | B2M | B2M | -4.092 | 0.002 | 0 | 0.003 | 0.005 | 0.007 | 0.068 |
| 9 | 9 | TB | TIMP1 | TIMP1 | -3.828 | 0.002 | 0 | 0.003 | 0.005 | 0.007 | 0.068 |
| 10 | 10 | TB | Fibrinogen | Fibrinogen | -3.712 | 0.002 | 0 | 0.003 | 0.005 | 0.007 | 0.068 |
| 11 | 11 | TB | ICAM.1 | ICAM.1 | -3.456 | 0.002 | 0 | 0.003 | 0.005 | 0.007 | 0.068 |
| 12 | 12 | TB | C3 | C3 | -3.213 | 0.002 | 0 | 0.003 | 0.005 | 0.007 | 0.068 |
| 13 | 17 | TB | TNFalpha | TNFalpha | -2.579 | 0.006 | 0.001 | 0.009 | 0.013 | 0.011 | 0.204 |
| 14 | 16 | TB | IL18 | IL18 | -2.716 | 0.012 | 0.005 | 0.018 | 0.023 | 0.019 | 0.407 |
| 15 | 20 | TB | vWF | vWF | -2.002 | 0.016 | 0.008 | 0.023 | 0.029 | 0.024 | 0.543 |
| 16 | 21 | TB | MMP9 | MMP9 | -1.552 | 0.156 | 0.133 | 0.177 | 0.252 | 0.207 | 1 |
| 17 | 24 | TB | VDBP | VDBP | -1.02 | 0.363 | 0.333 | 0.392 | 0.499 | 0.411 | 1 |
| 18 | 27 | TB | IFN.gamma | IFN.gamma | -0.741 | 0.493 | 0.461 | 0.523 | 0.621 | 0.511 | 1 |
| 19 | 28 | TB | MIP1.alpha | MIP1.alpha | -0.589 | 0.575 | 0.543 | 0.604 | 0.698 | 0.575 | 1 |
| 20 | 29 | TB | RANTES | RANTES | -0.567 | 0.609 | 0.578 | 0.638 | 0.714 | 0.588 | 1 |
| 21 | 32 | TB | Ferritin | Ferritin | -0.24 | 0.974 | 0.963 | 0.983 | 0.996 | 0.82 | 1 |
| 22 | 34 | TB | Eotaxin.1 | Eotaxin.1 | -0.013 | 0.996 | 0.991 | 0.999 | 0.996 | 0.82 | 1 |
| 23 | 13 | ILL | A2Macro | A2Macro | 3.184 | 0.002 | 0 | 0.003 | 0.005 | 0.007 | 0.068 |
| 24 | 14 | ILL | MMP2 | MMP2 | 2.886 | 0.006 | 0.001 | 0.009 | 0.013 | 0.011 | 0.204 |
| 25 | 15 | ILL | VCAM.1 | VCAM.1 | 2.767 | 0.006 | 0.001 | 0.009 | 0.013 | 0.011 | 0.204 |
| 26 | 18 | ILL | IL17 | IL17 | 2.526 | 0.012 | 0.005 | 0.018 | 0.023 | 0.019 | 0.407 |
| 27 | 19 | ILL | SCF | SCF | 2.345 | 0.024 | 0.014 | 0.032 | 0.041 | 0.034 | 0.814 |
| 28 | 22 | ILL | FactorVII | FactorVII | 1.228 | 0.248 | 0.22 | 0.273 | 0.383 | 0.315 | 1 |
| 29 | 23 | ILL | IL15 | IL15 | 1.092 | 0.261 | 0.233 | 0.288 | 0.387 | 0.318 | 1 |
| 30 | 25 | ILL | IL10 | IL10 | 0.982 | 0.367 | 0.337 | 0.396 | 0.499 | 0.411 | 1 |
| 31 | 26 | ILL | MCP1 | MCP1 | 0.834 | 0.401 | 0.37 | 0.431 | 0.525 | 0.432 | 1 |
| 32 | 30 | ILL | IL1ra | IL1ra | 0.485 | 0.639 | 0.608 | 0.667 | 0.724 | 0.596 | 1 |
| 33 | 31 | ILL | BDNF | BDNF | 0.277 | 0.796 | 0.77 | 0.82 | 0.873 | 0.719 | 1 |
| 34 | 33 | ILL | MIP1.beta | MIP1.beta | 0.226 | 0.93 | 0.913 | 0.945 | 0.988 | 0.813 | 1 |

Fig. 4B

| Row | Rank | Upregulated In | Feature | Description | maxT | FWER | Fold Change | ILL Mean | ILL Std | TB Mean | TB Std | k |
|---|---|---|---|---|---|---|---|---|---|---|---|---|
| 1 | 1 | TB | IL6 | IL6 | 0 | 0 | 2.92 | 7.381 | 8.499 | 21.554 | 13.636 | 1000 |
| 2 | 2 | TB | AAT | AAT | 0 | 0 | 1.416 | 2.181 | 0.799 | 3.089 | 0.67 | 1000 |
| 3 | 3 | TB | CRP | CRP | 0 | 0 | 3.415 | 24.671 | 41.378 | 84.255 | 57.741 | 1000 |
| 4 | 4 | TB | IL8 | IL8 | 0 | 0 | 2.097 | 6.809 | 4.775 | 14.28 | 8.268 | 1000 |
| 5 | 5 | TB | VEGF | VEGF | 0 | 0 | 1.432 | 222.283 | 79.051 | 318.286 | 94.803 | 1000 |
| 6 | 6 | TB | Haptoglobin | Haptoglobin | 0 | 0 | 2.41 | 1.567 | 1.633 | 3.775 | 2.794 | 1000 |
| 7 | 7 | TB | TNFR2 | TNFR2 | 0 | 0 | 1.44 | 5.577 | 2.598 | 8.033 | 3.215 | 1000 |
| 8 | 8 | TB | B2M | B2M | 0 | 0 | 1.267 | 1.366 | 0.408 | 1.731 | 0.52 | 1000 |
| 9 | 9 | TB | TIMP1 | TIMP1 | 0.002 | 0.003 | 1.346 | 64.604 | 27.832 | 86.964 | 33.052 | 1000 |
| 10 | 10 | TB | Fibrinogen | Fibrinogen | 0.004 | 0.006 | 1.402 | 4.625 | 1.582 | 6.486 | 3.381 | 1000 |
| 11 | 11 | TB | ICAM.1 | ICAM.1 | 0.006 | 0.009 | 1.655 | 79.497 | 69.096 | 131.589 | 87.612 | 1000 |
| 12 | 12 | TB | C3 | C3 | 0.023 | 0.032 | 1.194 | 0.743 | 0.229 | 0.887 | 0.239 | 1000 |
| 13 | 17 | TB | TNFalpha | TNFalpha | 0.102 | 0.189 | 1.6 | 2.174 | 1.922 | 3.479 | 3.231 | 998 |
| 14 | 16 | TB | IL18 | IL18 | 0.066 | 0.128 | 1.432 | 199.887 | 181.822 | 286.268 | 147.408 | 995 |
| 15 | 20 | TB | vWF | vWF | 0.369 | 0.614 | 1.544 | 9.396 | 6.973 | 14.512 | 17.725 | 993 |
| 16 | 21 | TB | MMP9 | MMP9 | 0.768 | 0.939 | 1.216 | 135.642 | 96.795 | 164.964 | 100.433 | 923 |
| 17 | 24 | TB | VDBP | VDBP | 0.981 | 1 | 1.106 | 141.377 | 90.152 | 156.357 | 59.077 | 819 |
| 18 | 27 | TB | IFN.gamma | IFN.gamma | 0.996 | 1 | 1.097 | 7.189 | 5.045 | 7.886 | 4.76 | 754 |
| 19 | 28 | TB | MIP1.alpha | MIP1.alpha | 0.999 | 1 | 1.132 | 19.67 | 27.238 | 22.264 | 17.391 | 713 |
| 20 | 29 | TB | RANTES | RANTES | 0.999 | 1 | 1.277 | 3.021 | 6.44 | 3.857 | 8.824 | 696 |
| 21 | 32 | TB | Ferritin | Ferritin | 1 | 1 | 1.114 | 222.868 | 734.144 | 248.261 | 240.434 | 487 |
| 22 | 34 | TB | Eotaxin.1 | Eotaxin.1 | 1 | 1 | 1.005 | 19.019 | 44.18 | 19.107 | 25.303 | 498 |
| 23 | 13 | ILL | A2Macro | A2Macro | 0.023 | 0.035 | 1.187 | 0.789 | 0.225 | 0.665 | 0.179 | 0 |
| 24 | 14 | ILL | MMP2 | MMP2 | 0.048 | 0.083 | 1.236 | 975.849 | 389.452 | 789.679 | 269.909 | 2 |
| 25 | 15 | ILL | VCAM.1 | VCAM.1 | 0.062 | 0.111 | 1.212 | 581.698 | 233.355 | 479.804 | 135.71 | 2 |
| 26 | 18 | ILL | IL17 | IL17 | 0.11 | 0.21 | 1.313 | 4.132 | 2.141 | 3.148 | 1.912 | 5 |
| 27 | 19 | ILL | SCF | SCF | 0.158 | 0.309 | 1.21 | 131.094 | 59.412 | 108.339 | 39.261 | 11 |
| 28 | 22 | ILL | FactorVII | FactorVII | 0.952 | 0.998 | 1.083 | 457.396 | 157.156 | 422.536 | 137.871 | 123 |
| 29 | 23 | ILL | IL15 | IL15 | 0.975 | 1 | 1.279 | 0.285 | 0.321 | 0.223 | 0.269 | 130 |
| 30 | 25 | ILL | IL10 | IL10 | 0.982 | 1 | 1.222 | 5.612 | 7.221 | 4.591 | 2.351 | 183 |
| 31 | 26 | ILL | MCP1 | MCP1 | 0.996 | 1 | 1.113 | 51.585 | 38.573 | 46.357 | 25.078 | 200 |
| 32 | 30 | ILL | IL1ra | IL1ra | 1 | 1 | 1.13 | 60.981 | 100.143 | 53.964 | 33.368 | 319 |
| 33 | 31 | ILL | BDNF | BDNF | 1 | 1 | 1.115 | 0.937 | 1.788 | 0.841 | 1.844 | 398 |
| 34 | 33 | ILL | MIP1.beta | MIP1.beta | 1 | 1 | 1.082 | 204.34 | 475.732 | 188.821 | 160.164 | 465 |

Fig. 4C

METHODS AND DEVICES FOR TUBERCULOSIS DIAGNOSIS USING BIOMARKER PROFILES

CROSS-REFERENCE TO RELATED APPLICATIONS

This application is a national stage filing under 35 U.S.C. §371 of International Application No. PCT/US2013/042620, filed May 24, 2013, which was published under PCT Article 21(2) in English, and which claims the benefit of U.S. Provisional Application No. 61/651,510, filed May 24, 2012, and U.S. Provisional Application No. 61/780,121, filed Mar. 13, 2013. The entire contents of each of these referenced applications are incorporated by reference herein.

BACKGROUND OF INVENTION

Nearly ten million people are newly infected with tuberculosis (TB) each year. Many of those newly infected are in developing or underdeveloped countries. Almost 2 million die from the disease; most of these deaths are preventable. The diagnosis of TB currently depends upon laboratory-based technology. The current diagnostic methods however fail to diagnose a significant portion of active TB cases. In addition, these methodologies typically require weeks to obtain results and may not even be available to patients who do not have ready access to the necessary testing facilities. Accurately diagnosing TB, including active TB, is necessary for controlling the spread of the infection.

SUMMARY OF INVENTION

The invention relates broadly to new approaches for diagnosing tuberculosis (TB) in subjects. The invention provides methods and devices for diagnosing TB in a subject based on particular biomarker profiles. The invention is premised, in part, on the unexpected finding that subjects having TB can be distinguished from other subjects, including subjects who present with TB-like symptoms but who are TB-negative, based on particular biomarker profiles. The biomarkers useful in distinguishing TB-positive from TB-negative subjects are IL-1RA, IL-6, IL-8, IL-17, IL-18, A2Macro, AAT, beta 2 macroglobulin (B2M), C3, CRP, Fibrinogen, Haptoglobin, ICAM-1, MMP-2, SCF, TIMP-1, TNF-alpha, TNFR2, VCAM-1, and VEGF. The invention contemplates using at least three biomarkers, including four biomarkers or five biomarkers, from the set of biomarkers to diagnose TB in subject.

Thus, in one aspect, the invention provides a method comprising:
(a) measuring levels, e.g., protein levels, of three or more biomarkers in a biological sample from a subject, wherein the biomarkers are selected from
  (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"); and/or
  (ii) a second group consisting of A2Macro, MMP-2, VCAM-1, IL-17, and SCF ("Group II biomarker");
(b) comparing the Group I and/or Group II biomarker levels with control levels; and
(c) identifying a subject with tuberculosis based on
  (i) Group I biomarker levels that are elevated in the biological sample compared to the control levels and/or
  (ii) Group II biomarker levels that are reduced in the biological sample compared to the control levels.

In some embodiments, the control levels are derived from tuberculosis-negative subjects having a persistent cough. TB-negative subjects may be identified as AFB-smear negative and/or MTB culture negative. A persistent cough would be a cough that has lasted for at least 2 weeks.

In some embodiments, the control levels are pre-determined.

In another aspect, the invention provides a method comprising:
(a) measuring levels, e.g., protein levels, of three or more biomarkers in a biological sample from a subject, wherein the biomarkers are selected from
  (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"); and/or
  (ii) a second group consisting of A2Macro, MMP-2, VCAM-1, IL-17, and SCF ("Group II biomarker");
(b) identifying a subject with tuberculosis based on
  (i) a Group I biomarker level that is above a pre-determined threshold, and/or
  (ii) a Group II biomarker level that is below a pre-determined threshold.

In some embodiments, the subject identified as TB-positive may be treated according to the standard of care, and/or the subject may be segregated from the population in order to reduce spread of the disease.

In some embodiments, the pre-determined threshold is a Group I or a Group II biomarker protein level from tuberculosis-negative subjects having a persistent cough.

In some embodiments, the three or more biomarkers are Group I biomarkers. In some embodiments, the three or more biomarkers are Group II biomarkers. In some embodiments, the three or more biomarkers are a combination of Group I biomarkers and Group II biomarkers. In some embodiments, the three or more biomarkers are selected from the group consisting of IL-18, IL-1RA, IL-6, IL-8, and VEGF. In some embodiments, the three or more biomarkers are selected from the group consisting of IL-18, IL-6, IL-8, and VEGF. In some embodiments, the three or more biomarkers are four biomarkers. In some embodiments, the three or more biomarkers are five biomarkers. Use of (a) one or more or (b) two or more biomarkers is also contemplated herein.

In some embodiments, the biological sample is a blood or serum sample.

In some embodiments, the tuberculosis is active tuberculosis. Subjects having active tuberculosis may be referred to herein as having TB-disease. Such subjects are considered contagious. In some embodiments, the subject has a persistent cough (i.e., a cough that has lasted for at least 2 weeks). In some embodiments, the subject is HIV-negative. In some embodiments, the subject is an adult.

In some embodiments, the protein levels are measured by an immuno-based assay (i.e., an immunoassay).

In some embodiments, the control level or the pre-determined threshold is selected from the group consisting of 7 pg/ml for IL-6, 2.5 mg/ml for AAT, 20 ug/ml for CRP, 8 pg/ml for IL-8, 250 pg/ml for VEGF, 1.5 mg/ml for Haptoglobin, 6 ng/ml for TNFR2, 1.4 ug/ml for B2M, 60 ng/ml for TIMP-1, 5 mg/ml for Fibrinogen, 60 ng/ml for ICAM-1, 0.7 mg/ml for C3, 2 pg/ml for TNF-alpha, 160 pg/ml for IL-18, and 40 pg/ml for IL-1RA, 3 pg/ml for IL-17, 750 ng/ml for MMP 2, 100 pg/ml for SCF, 0.6 mg/ml for A2Macro, and 450 ng/ml for VCAM-1.

In another aspect, the invention provides a method comprising:

(a) measuring levels, e.g., protein levels, of three or more biomarkers in a biological sample from a subject, wherein the biomarkers are selected from the group consisting of
  (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"); and/or
  (ii) a second group consisting of A2Macro, MMP-2, VCAM-1, IL-17, and SCF ("Group II biomarker"); and
(b) identifying a subject with tuberculosis based on
  (i) a Group I biomarker level that is above a pre-determined threshold, and/or
  (ii) a Group II biomarker level that is below a pre-determined threshold,
wherein the predetermined thresholds are set to yield a specificity greater than 50% and/or a sensitivity greater than 50%.

In some embodiments, the predetermined thresholds are set to yield a specificity greater than 90% regardless of sensitivity. In some embodiments, the predetermined thresholds are set to yield a sensitivity greater than 90% regardless of specificity. In some embodiments, the predetermined thresholds are set to yield a sensitivity greater than 75% and a specificity greater than 75%. In some embodiments, the predetermined thresholds are set to yield a sensitivity greater than 90% and/or a specificity greater than 90%.

In another aspect, the invention provides a device comprising a sample inlet and binding partners for three or more biomarkers selected from the group consisting of
  (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"), and/or
  (ii) a second group consisting of A2Macro, MMP-2, VCAM-1, IL-17, and SCF ("Group II biomarker"),
wherein the binding partners are grouped together on a substrate based on biomarker specificity and groups are physically separated from each other on the substrate.

In some embodiments, the three or more biomarkers are four biomarkers. In some embodiments, the three or more biomarkers are five biomarkers. Use of (a) one or more or (b) two or more biomarkers is also contemplated herein.

In some embodiments, the three or more markers are Group I biomarkers. In some embodiments, the three or more biomarkers are Group II biomarkers. In some embodiments, the three or more biomarkers are a combination of Group I biomarkers and Group II biomarkers. In some embodiments, the three or more biomarkers are selected from the group consisting of IL-18, IL-1RA, IL-6, IL-8, and VEGF. In some embodiments, the three or more biomarkers are selected from the group consisting of IL-18, IL-6, IL-8, and VEGF.

In some embodiments, the binding partners are biomarker-specific antibodies or antibody fragments. In some embodiments, the binding partners are biomarker-specific ligands or receptors. In some embodiments, the binding partners are aptamers.

In some embodiments, the device further comprises microfluidic channels.

It is to be understood that the various foregoing aspects and embodiments of the invention may be combined in a number of ways, unless explicitly stated otherwise.

These and other aspects and embodiments of the invention will be described herein in greater detail.

BRIEF DESCRIPTION OF DRAWINGS

FIG. 2 is a series of box plots depicting the raw data obtained for each biomarker in TB subjects (left box in each box plot) or control (ill) subjects (right box in each box plot).

FIGS. 4B and 4C are a table depicting the biomarkers upregulated in TB or in control (ill) subjects.

Figure 1:
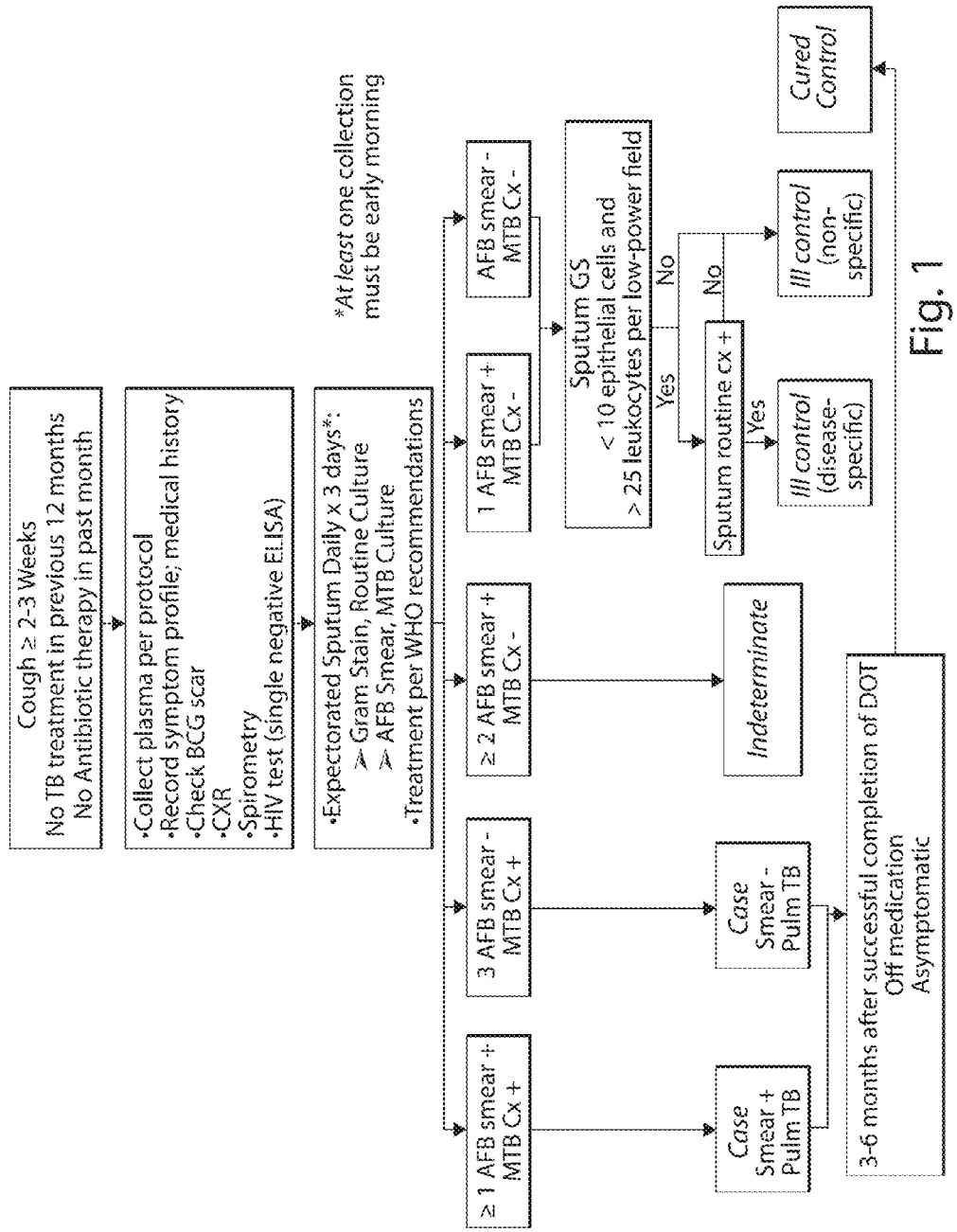
FIG. 1 is a flow chart depicting the selection process for subjects and the sample collection process for the TB study cohort.
Figure 2A:
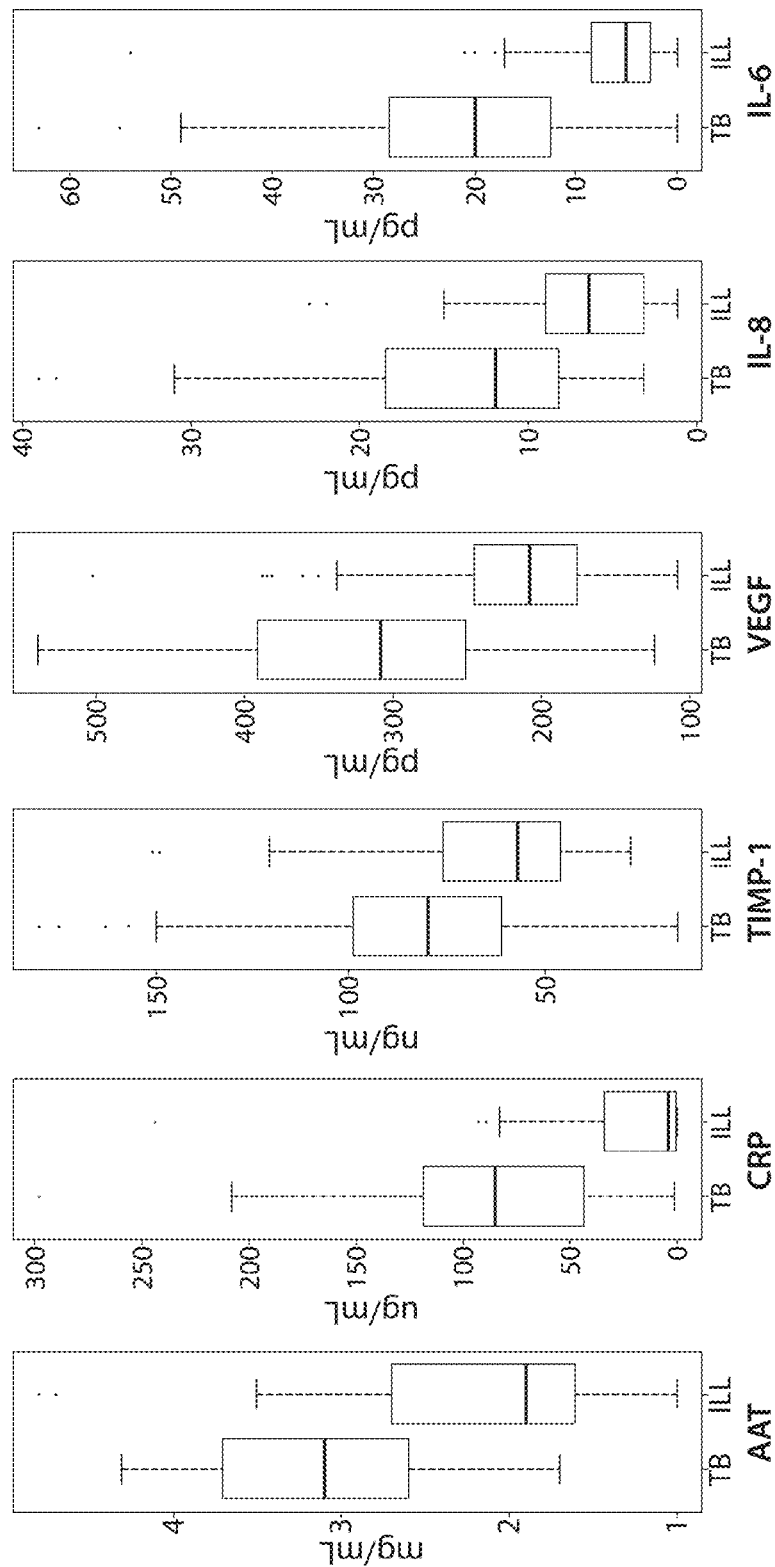
FIG. 2A depicts box plots for AAT, CRP, TIMP-1, VEGF, IL-8, and IL-6. The y-axis labels for AAT, CRP, TIMP-1, VEGF, IL-8, AND IL-6 are mg/mL, µg/mL, ng/mL, pg/mL, pg/mL, and pg/mL, respectively.
Figure 2B:
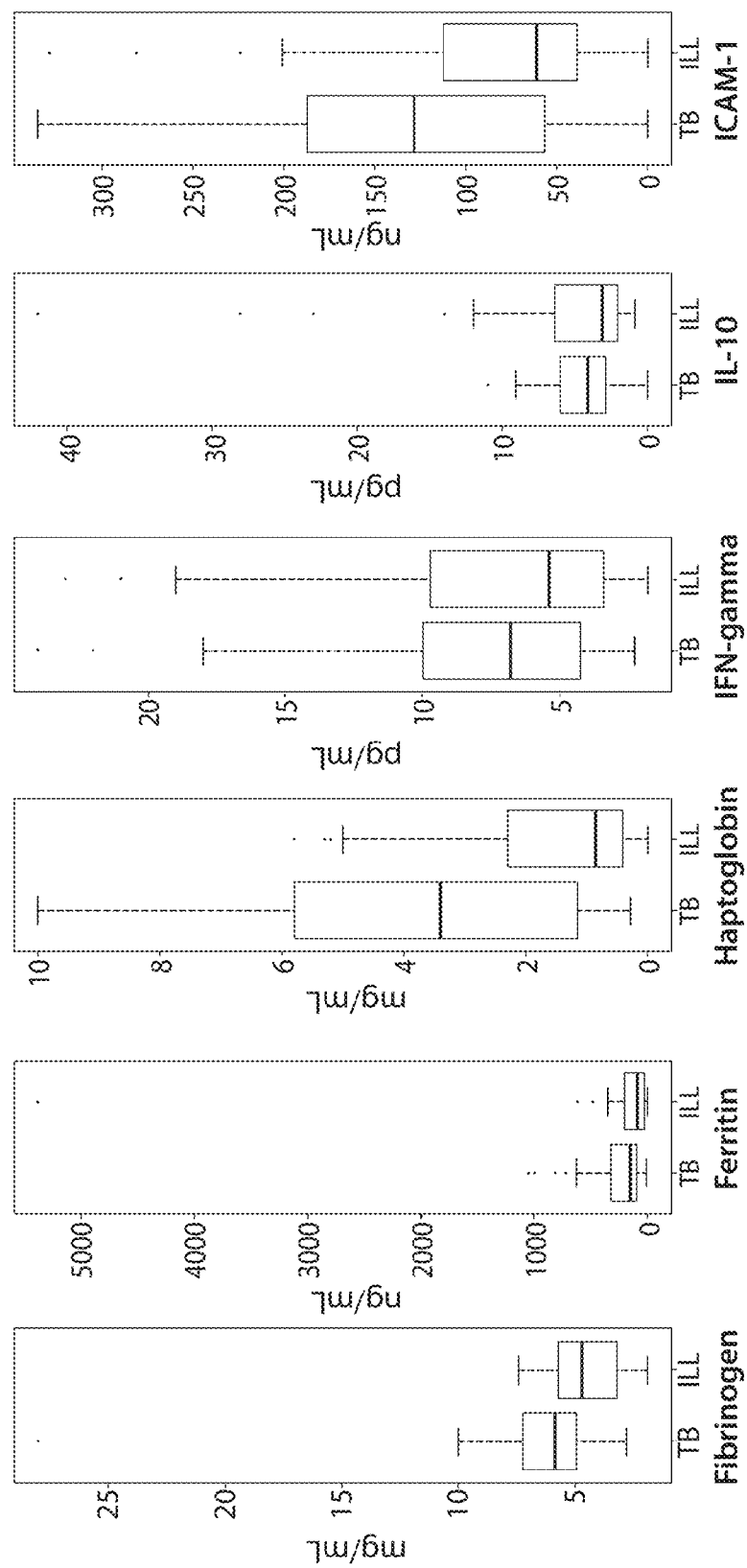
FIG. 2B depicts box plots for Fibrinogen, Ferritin, Haptoglobin, INF-gamma, IL-10, and ICAM-1. The y-axis labels for Fibrinogen, Ferritin, Haptoglobin, INF-gamma, IL-10, and ICAM-1 are mg/mL, ng/mL, mg/mL, pg/mL, pg/mL, and ng/mL, respectively.
Figure 2C:
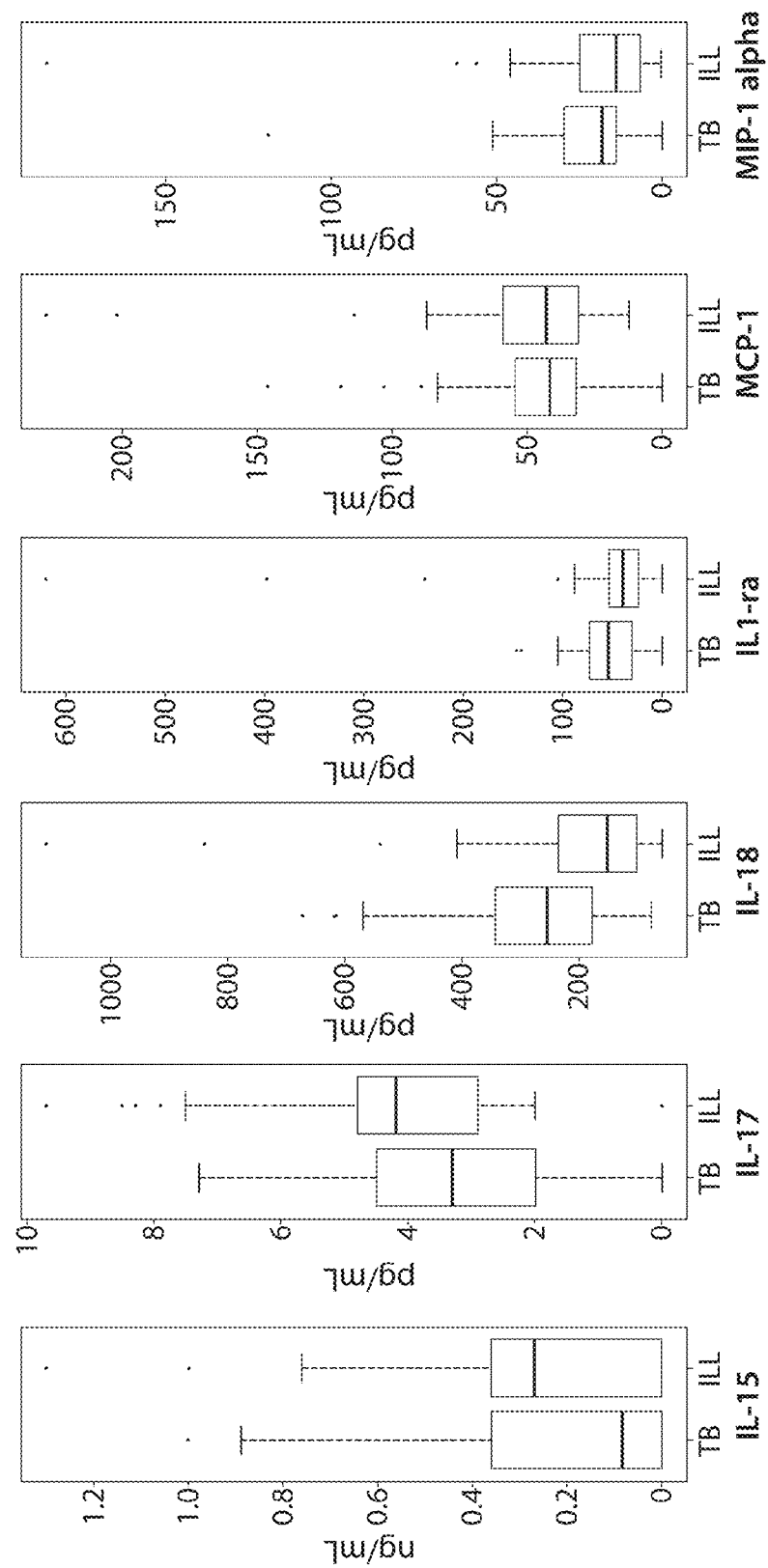
FIG. 2C depicts box plots for IL-15, IL-17, IL-18, IL-1RA, MCP-1, and MIP-1 alpha. The y-axis labels for IL-15, IL-17, IL-18, IL-1RA, MCP-1, and MIP-1 alpha are ng/mL, pg/mL, pg/mL, pg/mL, pg/mL, and pg/mL, respectively.
Figure 2D:
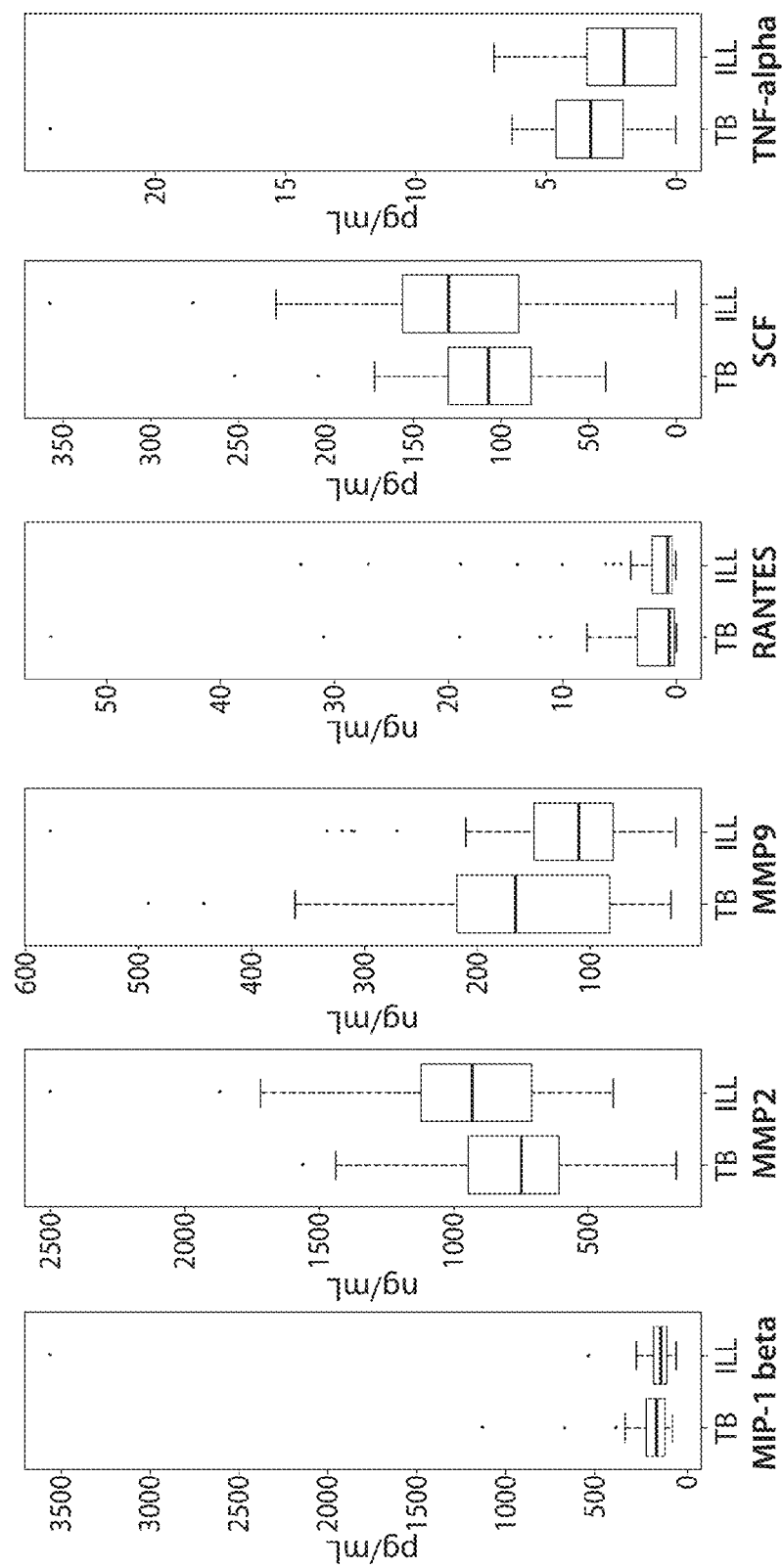
FIG. 2D depicts box plots for MIP-1 beta, MMP-2, MMP-9, RANTES, SCF, and TNF-alpha. The y-axis labels for MIP-1 beta, MMP-2, MMP-9, RANTES, SCF, and TNF-alpha are pg/mL, ng/mL, ng/mL, ng/mL, pg/mL, and pg/mL, respectively.
Figure 2E:
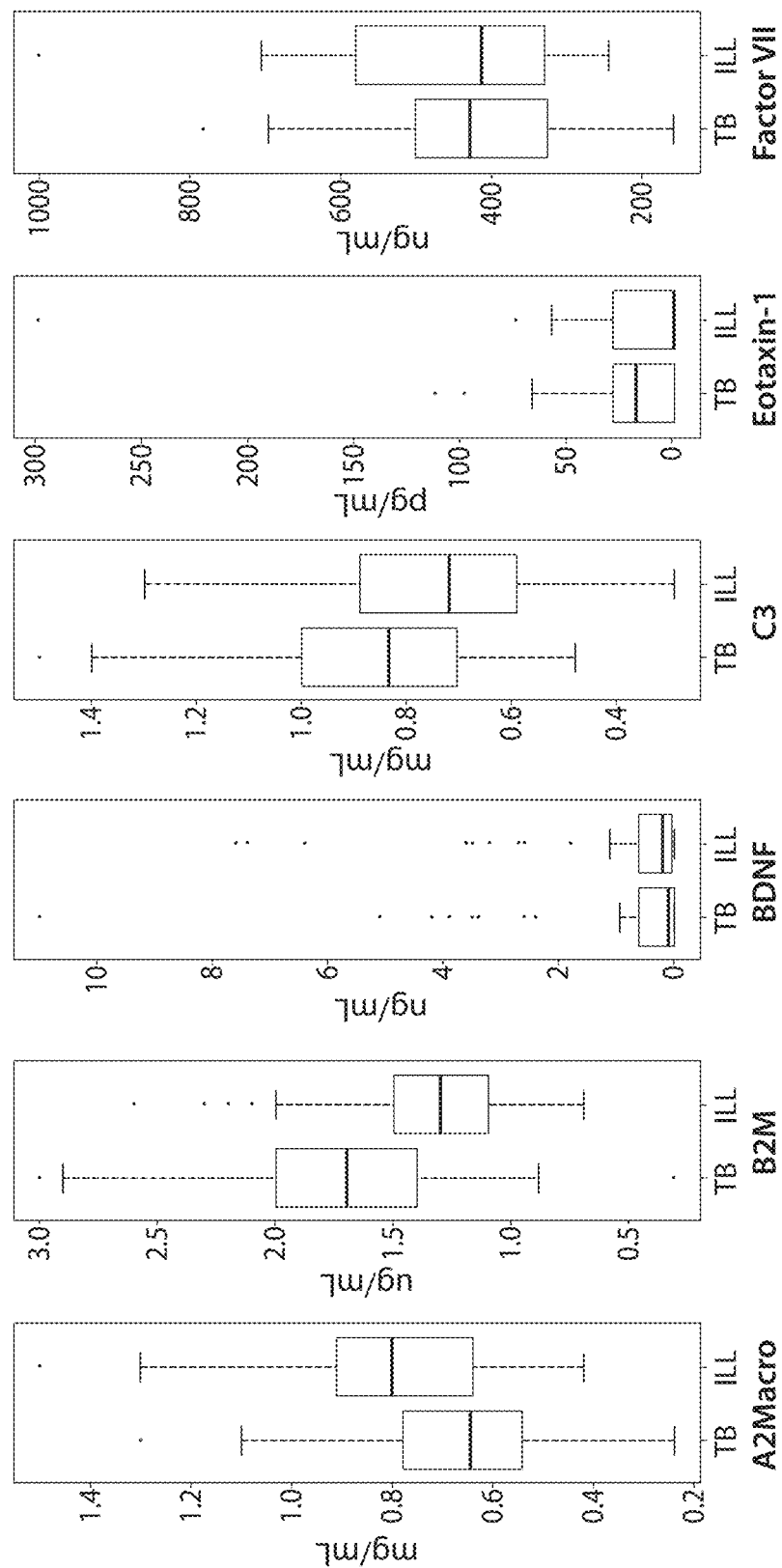
FIG. 2E depicts box plots for A2Macro, B2M, BDNF, C3, Eotaxin-1, and Factor VII. The y-axis labels for A2Macro, B2M, BDNF, C3, Eotaxin-1, and Factor VII are mg/mL, µg/mL, ng/mL, mg/mL, pg/mL, and ng/mL, respectively.
Figure 2F:
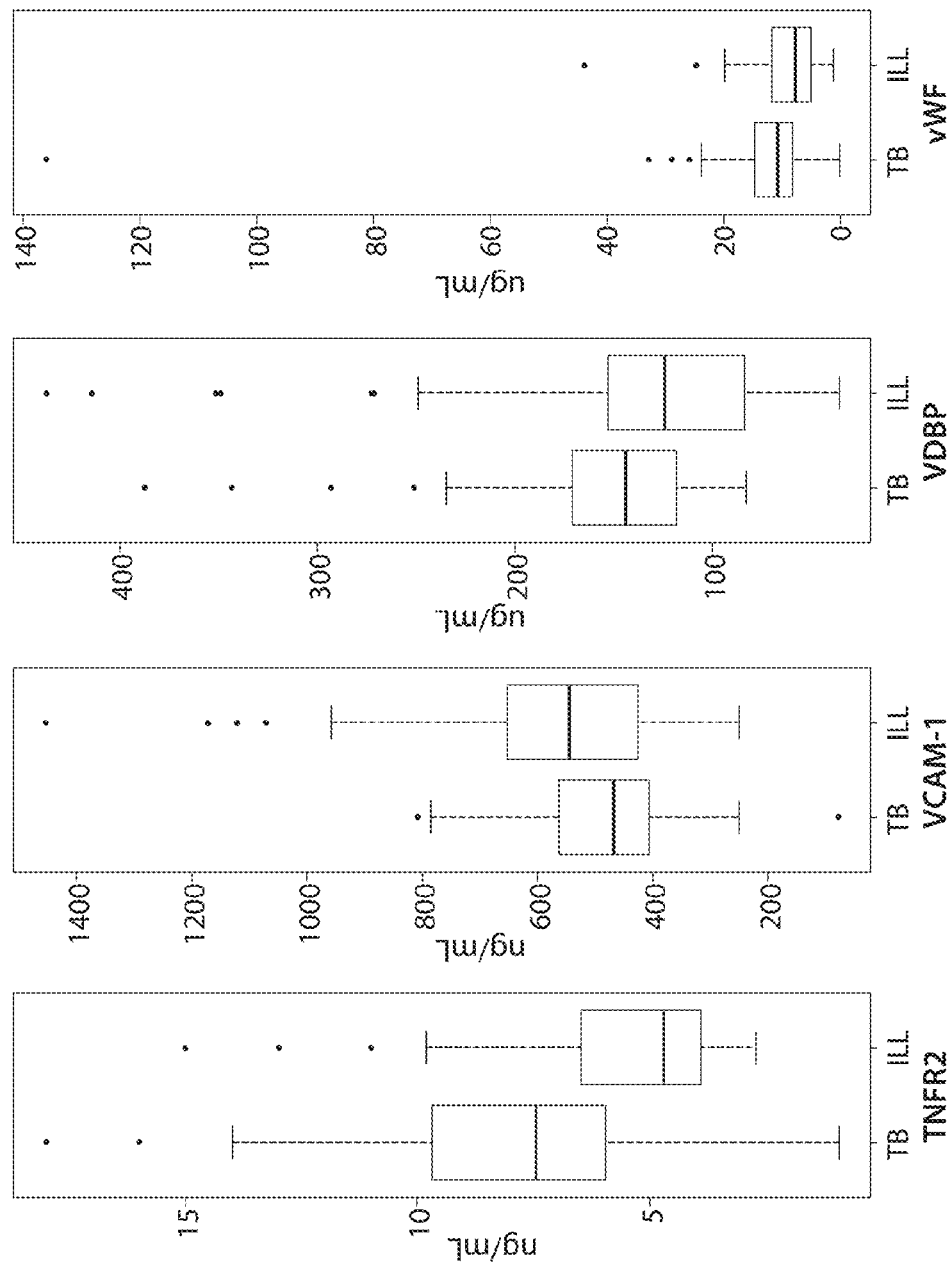
FIG. 2F depicts box plots for TNFR2, VCAM-1, VDBP, and vWF. The y-axis labels for TNFR2, VCAM-1, VDBP, and vWF are ng/mL, ng/mL, µg/mL, and µg/mL, respectively.

It is to be understood that the Figures are not required for enablement of the invention.

DETAILED DESCRIPTION OF INVENTION

The invention provides methods and devices for diagnosing tuberculosis (TB). The current gold standard assay for diagnosing TB is Sputum Smear Microscope (SSM). This technique involves obtaining three sputum samples from a subject over the course of several days. The need to provide sputum samples on several days limits participation by subjects, resulting in incomplete and/or inaccurate tests. The need to provide a sputum sample also poses problems for younger subjects such as infants, toddler and younger children. In addition to these compliance issues, the SSM has been shown to suffer from sensitivity issues as well. For example, although it is able to achieve specificity levels that are greater than 95% in some circumstances, in field settings it has demonstrated sensitivity at levels below 50%. In some instances, its sensitivity can be less than 30%. This is particularly true if the tested subject is both TB-positive and HIV-positive.

In contrast, the invention provides a rapid diagnostic that requires a single sample that may be obtained from virtually any subject. The diagnostic method of the invention has been shown to be robust and capable of achieving sensitivity and specificity levels of equal to greater than 90%. The method requires little if any infrastructure to diagnose TB and thus is particularly amenable to settings where laboratory resources and infrastructure are scarce or non-existent.

The methods of the invention diagnose TB in a subject based on particular biomarker profiles. It has been discovered, in accordance with the invention, that subjects having TB can be distinguished from other subjects including those who present with TB-like symptoms (e.g., a persistent cough) yet are TB-negative. The biomarkers are all biomarkers associated with a host immune response. The levels of some of these biomarkers are increased in TB-positive subjects, while the levels of others are decreased in TB-positive subjects relative to controls.

The ability to readily diagnose a subject having TB allows for segregation of the subject away from the general population and/or treatment of the subject with an anti-TB therapeutic agent. Accordingly, the diagnostic methods provided herein can be used to identify subjects who should be physically separated from the general population, possibly quarantined, and/or treated with an anti-TB therapeutic agent. Importantly, the methods and devices of the invention provide for robust discrimination between subjects that are TB-positive and TB-negative.

These methods and devices that may be used to perform such methods will be described in greater detail herein.

Additionally, the methods and devices of the invention may be used to monitor response to an anti-TB therapeutic agent and/or indicate that subject is in need of further anti-TB therapeutic agent.

Biomarkers

The biomarkers of the invention are a select group of biomarkers associated with a host immune response. These biomarkers were identified, as described in the Examples, by analyzing protein profiles in subjects presenting with a persistent cough without knowledge of TB status. Protein profiles from these subjects were then grouped based on consistent patterns of upregulated or downregulated biomarkers. Such patterns correlated with the TB status of the subject.

More specifically, a number of biomarkers were found to be upregulated (or to have elevated levels, as the terms are used interchangeably) relative to controls. As used herein, an upregulated or elevated level includes a level that is above a control level or pre-determined threshold as defined herein. An upregulated or elevated level may be, for example, 1%, 5%, 10%, 20%, 30%, 40%, 50%, 60%, 70%, 80%, 90%, 100%, 150%, 200%, 300%, 400%, 500% or more above a control level or pre-determined threshold as defined herein. These "upregulated" biomarkers are AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF. They are referred to herein as Group I biomarkers. The GenBank Accession Nos. for these biomarkers are shown in Table 1 and Table 2. The Group I biomarkers may be ranked according to their level of fold-expression over controls (i.e., expression in TB-positive subject/expression in TB-negative ill control). The descending order of fold-expression over control is as follows (i.e., highest fold increase to lowest fold increase): IL-6, AAT, CRP, IL-8, VEGF, Haptoglobin, TNFR2, beta-2-macroglobulin, TIMP-1, Fibrinogen, ICAM-1, C3, TNF-alpha, IL-18 and IL-1RA.

A number of other biomarkers were found to be downregulated (or to have reduced levels, as the terms are used interchangeably herein) relative to control levels. These "downregulated" biomarkers are A2Macro, MMP-2, VCAM-1, IL-17, and SCF. They are referred to herein as Group II biomarkers. The GenBank Accession Nos. for these biomarkers are shown in Table 1 and Table 2. The Group II biomarkers may be ranked according to their level of fold-expression relative to controls as follows: A2Macro, MMP-2, VCAM-1, IL-17, and SCF.

TABLE 1

GenBank Accession Numbers for Biomarker Protein Sequences

| Biomarker | GenBank Accession Numbers |
|---|---|
| IL-1RA | NP_000568.1, NP_776213.1, NP_776214.1, NP_776215.1 |
| IL-6 | NP_000591.1 |
| IL-8 | NP_000575.1 |
| IL-18 | NP_001230140.1, NP_001553.1 |
| VEGF | NP_001020537.2, NP_001020538.2, NP_001020539.2, NP_001020540.2, NP_001020541.2, NP_001028928.1, |

TABLE 1-continued

GenBank Accession Numbers for Biomarker Protein Sequences

| Biomarker | GenBank Accession Numbers |
|---|---|
|  | NP_001165093.1, NP_001165094.1, |
|  | NP_001165095.1, NP_001165096.1, |
|  | NP_001165097.1, NP_001165098.1, |
|  | NP_001165099.1, NP_001165100.1, |
|  | NP_001165101.1, NP_001191313.1, |
|  | NP_001191314.1, NP_003367.4 |
| AAT | NP_000286.3, NP_001002235.1, |
|  | NP_001002236.1, NP_001121172.1, |
|  | NP_001121173.1, NP_001121174.1, |
|  | NP_001121175.1, NP_001121176.1, |
|  | NP_001121177.1, NP_001121178.1, |
|  | NP_001121179.1 |
| CRP | NP_000558.2 |
| Haptoglobin | NP_001119574.1, NP_005134.1 |
| TNFR2 | NP_001057.1 |
| B2M | NP_004039.1 |
| TIMP-1 | NP_003245.1 |
| Fibrinogen | NP_000499.1, NP_068657.1, NP_001171670.1, |
|  | NP_005132.2, NP_000500.2, NP_068656.2 |
| ICAM-1 | NP_000192.2 |
| C3 | NP_000055.2 |
| TNF-alpha | NP_000585.2 |
| A2Macro | NP_000005.2 |
| MMP-2 | NP_001121363.1, NP_004521.1 |
| VCAM-1 | NP_001069.1, NP_001186763.1, NP_542413.1 |
| IL-17 | NP_002181.1 |
| SCF | NP_000890.1, NP_003985.2 |

TABLE 2

GenBank Accession Numbers for Biomarker Nucleotide Sequences

| Biomarker | Genbank Accession Numbers |
|---|---|
| IL-1RA | NM_000577.4, NM_173841.2, NM_173842.2, |
|  | NM_173843.2 |
| IL-6 | NM_000600.3 |
| IL-8 | NM_000584.3 |
| IL-18 | NM_001243211.1, NM_001562.3 |
| VEGF | NM_001025366.2, NM_001025367.2, |
|  | NM_001025368.2, NM_001025369.2, |
|  | NM_001025370.2, NM_001033756.2, |
|  | NM_001171622.1, NM_001171623.1, |
|  | NM_001171624.1, NM_001171625.1, |
|  | NM_001171626.1, NM_001171627.1, |
|  | NM_001171628.1, NM_001171629.1, |
|  | NM_001171630.1, NM_001204384.1, |
|  | NM_001204385.1, NM_003376.5 |
| AAT | NM_000295.4, NM_001002235.2, |
|  | NM_001002236.2, NM_001127700.1, |
|  | NM_001127701.1, NM_001127702.1, |
|  | NM_001127703.1, NM_001127704.1, |
|  | NM_001127705.1, NM_001127706.1, |
|  | NM_001127707.1 |
| CRP | NM_000567.2 |
| Haptoglobin | NM_001126102.1, NM_005143.3 |
| TNFR2 | NM_001066.2 |
| B2M | NM_004048.2 |
| TIMP-1 | NM_003254.2 |
| Fibrinogen | NM_000508.3, NM_021871.2, NM_001184741.1, |
|  | NM_005141.4, NM_000509.4, NM_021870.2 |
| ICAM-1 | NM_000201.2 |
| C3 | NM_000064.2 |
| TNF-alpha | NM_000594.2 |
| A2Macro | NM_000014.4 |
| MMP-2 | NM_001127891.1, NM_004530.4 |
| VCAM-1 | NM_001078.3, NM_001199834.1, NM_080682.2 |
| IL-17 | NM_002190.2 |
| SCF | NM_000899.4, NM_003994.5 |

It has been found, in accordance with the invention, that robust discrimination between TB-positive and TB-negative samples can be achieved using as few as three of any of the foregoing biomarkers. Thus, in some instances, the methods and devices measure three biomarkers. In other instances, the methods and devices measure more than three biomarkers (e.g., 4, 5, 6, 7, 8, 9, 10, 11, 12, 13, 14, 15, 16, 17, 18, 19, or 20 biomarkers). The biomarkers may be Group I biomarkers, or they may be Group II biomarkers, or they may be a combination of Group I biomarkers and Group II biomarkers.

In some instances, it may be important to select biomarkers that are in a similar dynamic range. This means that biomarkers may be selected based on their concentration in the samples being tested such that all the biomarkers used in a particular method have a concentration in a particular range. As an example, such a range may be a pg/ml range, or a ng/ml range, or a µg/ml range, or a mg/ml range. A pg/ml range means a detectable concentration range up to 1000 pg/ml. A ng/ml range means a detectable concentration range of 1-1000 ng/ml. A µg/ml range means a detectable concentration range of 1-1000 µg/ml. A mg/ml range means a detectable concentration range of 1-1000 mg/ml. In some instances, the dynamic range spans the µg/ml and mg/ml ranges.

The biomarkers used herein have been reported to have concentration ranges in plasma in normal subjects as follows: A2Macro (0.24-1.5 mg/ml), AAT (1-4.8 mg/ml), C3 (0.29-1.5 mg/ml), Fibrinogen (1.9-28 mg/ml), Haptoglobin (0.046-10 mg/ml), B2M (0.31-3 µg/ml), CRP (0.072-298 µg/ml), MMP-2 (173-2500 ng/ml), TIMP-1 (16-180 ng/ml), TNFR2 (0.93-18 ng/ml), VCAM-1 (78-1450 ng/ml), ICAM-1 (0.44-335 ng/ml), IL-17 (2-9.7 pg/ml), IL-18 (58-3110 pg/ml), IL-1RA (24-620 pg/ml), IL-6 (1.4-63 pg/ml), IL-8 (1.2-39 pg/ml), SCF (40-357 pg/ml), TNF-alpha (1.2-24 pg/ml), and VEGF (109-538 pg/ml).

Accordingly, it is to be understood that the invention contemplates a variety of biomarker subsets including, without limitation, any combination of three or more of the following biomarkers:

1. IL-17, IL-18, IL-1RA, IL-6, IL-8, SCF, TNF-alpha, and VEGF;
2. IL-18, IL-1RA, IL-6, IL-8, TNF-alpha, and VEGF;
3. IL-18, IL-1RA, IL-6, IL-8, and VEGF;
4. ICAM-1, MMP-2, TIMP-1, TNFR2, and VCAM-1;
5. ICAM-1, TIMP-1, and TNFR2;
6. TIMP-1, VCAM-1, ICAM-1, and MMP-2;
7. CRP, AAT, Haptoglobin, Fibrinogen, A2Macro, TNFR2, C3, and beta-2-macroglobulin;
8. A2macro, AAT, Fibrinogen, Haptoglobin, C3, beta-2-macroglobulin, and CRP;
9. AAT, Fibrinogen, Haptoglobin, C3, beta-2-macroglobulin, and CRP;
10. AAT, Fibrinogen, Haptoglobin, and C3; and
11. IL-18, IL-6, IL-8, and VEGF.

In some embodiments, the methods and/or devices measure IL-18, IL-1RA, IL-6, IL-8, and VEGF levels. In some embodiments, the methods and/or devices measure IL-18, IL-6, IL-8, and VEGF levels. In some embodiments, the methods and/or devices measure TIMP-1, VCAM-1, ICAM-1, and MMP-2 levels. In some embodiments, the methods and/or devices measure CRP, AAT, Haptoglobin, Fibrinogen, A2Macro, TNFR2, C3, and beta-2-macroglobulin levels.

The following is a list of biomarkers in order of decreasing discriminatory power: IL-6, VEGF, AAT, CRP, IL-1RA, TIMP-1, IL-8, IL-18, A2Macro, Haptoglobin, ICAM-1, VCAM-1, SCF, IL-17, Fibrinogen, beta-2-macroglobulin, TNF-alpha, C3, TNFR2, and MMP-2. It is to be understood that this order will depend upon the other biomarkers in the set as on the classification model or algorithm used to analyze the biomarkers in the set. Therefore if the set is complete (i.e., all 20 biomarkers), then the order shown above is accurate. If however a subset of the 20 biomarkers is used, then their relative discriminatory power (and thus order) may change. Examples of subsets and the order of discriminatory power between members of the subsets are as follows:

1. IL-6, VEGF, AAT, CRP, IL-1RA, TIMP-1, IL-8, IL-18, A2Macro, Haptoglobin, ICAM-1, VCAM-1, SCF, IL-17, Fibrinogen, and beta-2-macroglobulin;
2. IL-6, VEGF, AAT, CRP, IL-1RA, TIMP-1, IL-8, IL-18, A2Macro, and Haptoglobin;
3. IL-6, VEGF, CRP, AAT, TIMP-1, IL-8, and IL-1RA;
4. IL-6, VEGF, AAT, CRP, and TIMP-1;
5. IL-6, VEGF, IL-18 and IL-8;
6. IL-6, VEGF, IL-18, IL-8, and IL-1RA;
7. TIMP-1, VCAM-1, ICAM-1, and MMP2;
8. CRP, AAT, Haptoglobin, Fibrinogen, A2Macro, TNFR2, C3 and beta-2-macroglobulin.

Based on these rank orders of decreasing discriminatory power, it will be understood that some methods will measure three or more biomarkers provided that one of the biomarkers is IL-6, or TIMP-1, or CRP.

Some methods will measure three or more biomarkers wherein two of the biomarkers are IL-6 and VEGF, or IL-6 and AAT, or TIMP-1 and VCAM-1, or CRP and AAT.

Some methods will measure three or more biomarkers wherein three of the biomarkers are IL-6, VEGF and AAT, or IL-6, VEGF and CRP, or IL-6, VEGF and IL-18, or TIMP-1, VCAM-1, and ICAM-1, or CRP, AAT and Haptoglobin.

Some methods will measure four or more biomarkers wherein four of the biomarkers are IL-6, VEGF, AAT and CRP, IL-6, VEGF, IL-18 and IL-8, or TIMP-1, VCAM-1, ICAM-1 and MMP-2, or CRP, AAT, Haptoglobin, and Fibrinogen.

Some methods will measure five or more biomarkers wherein five of the biomarkers are IL-6, VEGF, AAT, CRP and IL-1RA, or IL-6, VEGF, AAT, CRP and TIMP-1, or IL-6, VEGF, IL-18, IL-8 and IL-1RA, or CRP, AAT, Haptoglobin, Fibrinogen and A2Macro.

Some methods will measure six or more biomarkers wherein six of the biomarkers are IL-6, VEGF, AAT, CRP, IL-1RA and TIMP-1, or IL-6, VEGF, AAT, CRP, TIMP-1 and IL-8, or CRP, AAT, Haptoglobin, Fibrinogen, A2Macro and TNFR2.

Some methods will measure seven or more biomarkers wherein seven of the biomarkers are IL-6, VEGF, AAT, CRP, IL-1RA, TIMP-1 and IL-8, or IL-6, VEGF, AAT, CRP, TIMP-1, IL-8 and IL-1RA, or CRP, AAT, Haptoglobin, Fibrinogen, A2Macro, TNFR2 and C3.

Some methods will measure eight or more biomarkers wherein eight of the biomarkers are IL-6, VEGF, AAT, CRP, IL-1RA, TIMP-1, IL-8 and IL-18, or CRP, AAT, Haptoglobin, Fibrinogen, A2Macro, TNFR2, C3 and beta-2-macroglobulin.

Some methods will measure nine or more biomarkers wherein nine of the biomarkers are IL-6, VEGF, AAT, CRP, IL-1RA, TIMP-1, IL-8, IL-18 and A2Macro.

Some methods will measure ten or more biomarkers wherein ten of the biomarkers are IL-6, VEGF, AAT, CRP, IL-1RA, TIMP-1, IL-8, IL-18, A2Macro and Haptoglobin.

Some methods will measure eleven or more biomarkers wherein eleven of the biomarkers are IL-6, VEGF, AAT, CRP, IL-1RA, TIMP-1, IL-8, IL-18, A2Macro, Haptoglobin and ICAM-1.

Some methods will measure twelve or more biomarkers wherein twelve of the biomarkers are IL-6, VEGF, AAT, CRP, IL-1RA, TIMP-1, IL-8, IL-18, A2Macro, Haptoglobin ICAM-1 and VCAM-1.

Some methods will measure 13 or more biomarkers wherein 13 of the biomarkers are IL-6, VEGF, AAT, CRP, IL-1RA, TIMP-1, IL-8, IL-18, A2Macro, Haptoglobin ICAM-1, VCAM-1 and SCF.

Some methods will measure 14 or more biomarkers wherein 14 of the biomarkers are IL-6, VEGF, AAT, CRP, IL-1RA, TIMP-1, IL-8, IL-18, A2Macro, Haptoglobin ICAM-1, VCAM-1, SCF and IL-17.

Some methods will measure 15 or more biomarkers wherein 15 of the biomarkers are IL-6, VEGF, AAT, CRP, IL-1RA, TIMP-1, IL-8, IL-18, A2Macro, Haptoglobin ICAM-1, VCAM-1, SCF, IL-17 and Fibrinogen.

Some methods will measure 16 or more biomarkers wherein 16 of the biomarkers are IL-6, VEGF, AAT, CRP, IL-1RA, TIMP-1, IL-8, IL-18, A2Macro, Haptoglobin ICAM-1, VCAM-1, SCF, IL-17, Fibrinogen and beta-2-macroglobulin.

Some methods will measure 17 or more biomarkers wherein 17 of the biomarkers are IL-6, VEGF, AAT, CRP, IL-1RA, TIMP-1, IL-8, IL-18, A2Macro, Haptoglobin ICAM-1, VCAM-1, SCF, IL-17, Fibrinogen, beta-2-macroglobulin and TNF-alpha.

Some methods will measure 18 or more biomarkers wherein 18 of the biomarkers are IL-6, VEGF, AAT, CRP, IL-1RA, TIMP-1, IL-8, IL-18, A2Macro, Haptoglobin ICAM-1, VCAM-1, SCF, IL-17, Fibrinogen, beta-2-macroglobulin, TNF-alpha and C3.

Some methods will measure 19 or more biomarkers wherein 19 of the biomarkers are IL-6, VEGF, AAT, CRP, IL-1RA, TIMP-1, IL-8, IL-18, A2Macro, Haptoglobin ICAM-1, VCAM-1, SCF, IL-17, Fibrinogen, beta-2-macroglobulin, TNF-alpha, C3 and TNFR2.

Diagnostic, Prognostic, Theranostic, and Treatment Methods

The methods and devices of the invention have many uses. For example, the methods and devices provided herein may be used for diagnosis, such as identifying a subject having TB. In some embodiments, the subject identified as having TB may be segregated away from the general population. Accordingly, in some embodiments, methods of the invention comprise a step of segregating from the general population a subject identified as having TB. Such segregation/isolation may involve, for example, quarantine of the subject.

In another example, the methods and devices provided herein may be used for theranostic purposes, such as selection of a subject for treatment with an anti-TB therapeutic agent. Such theranostic methods help to avoid administration of a medicament or therapy to subjects that are ill and outwardly manifest as potentially having TB but do not have TB. As a result, fewer resources are spent on unnecessary treatment, which may be especially important in developing countries. Reduction of unnecessary treatment may also help to prevent the development of treatment-resistant strains of TB.

Accordingly, in some embodiments, methods of the invention comprise a step of treating a subject identified as having TB with an anti-TB therapeutic agent. In some embodiments, the method comprises:

(a) selecting a subject for treatment with an anti-TB therapeutic agent on the basis that the subject has an elevated level of one or more of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF and/or a reduced level of one or more of A2Macro, MMP-2, VCAM-1, IL-17, and SCF; and (b) administering an anti-TB therapeutic agent to a subject having an elevated level of one or more of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF and/or a reduced level of one or more of A2Macro, MMP-2, VCAM-1, IL-17, and SCF. In some embodiments, the level is a protein level. In some embodiments, one or more is two or more. In some embodiments, one or more is three or more.

In some embodiments, methods of the invention are methods of treatment. As used herein, treatment includes reducing symptoms of TB, reducing TB load, and/or eradication of a TB infection. In some embodiments, a method of treatment comprises administering an effective amount of an anti-TB therapeutic agent to a subject identified as having TB based on levels of three or more biomarkers as described herein.

Anti-TB therapeutic agents are well known in the art (see, e.g., Treatment of tuberculosis—guidelines for national programmes, 3rd ed. Geneva, World Health Organization and Guidelines for the programmatic management of drug-resistant tuberculosis. Geneva, World Health Organization, 2006).

In some embodiments, an anti-TB therapeutic agent comprises one or more antibiotics. Exemplary antibiotics for treatment of TB include, but are not limited to, Isoniazid, Rifampin (Rifadin, Rimactane), Rifapentine, Ethambutol (Myambutol), Streptomycin, and Pyrazinamide. Other exemplary antibiotics include kanamycin, amikacin, capreomycin, levofloxacin, moxifloxacin, gatifloxacin, ofloxacin, ethionamide, prothionamide, cycloserine, terizidone, p-aminosalicylic acid, clofazimine, linezolid, amoxicillin/clavulanate, thioacetazone, clarithromycin, bedaquiline, and imipenem. In some embodiments, an anti-TB therapeutic agent comprises aminoglycoside or capreomycin. In some embodiments, more than one anti-TB therapeutic agent is administered in combination (either together or separately) to a subject. In some embodiments, two, three, four, five or more anti-TB therapeutic agents may be administered. In some embodiments, at least four anti-TB therapeutic agents are administered.

Administration of an anti-TB therapeutic agent may be accomplished by any method known in the art (see, e.g., Harrison's Principle of Internal Medicine, McGraw Hill Inc. 17$^{th}$ Edition, Mar. 6, 2008, Eds. Fauci et al.). Administration may be local or systemic. Administration may be parenteral (e.g., intravenous, subcutaneous, or intradermal) or oral. Compositions for different routes of administration are well known in the art (see, e.g., Remington's Pharmaceutical Sciences, 1965, XIII Edition, Mack Publishing Co., Ed. by E. W. Martin). Dosage will depend on the subject, the treatment, and the route of administration. Dosage can be determined by the skilled artisan.

The duration of administration will also depend on the anti-TB therapeutic agent to be administered and the severity of the TB infection in the subject and the type of TB infection (e.g., drug-resistant TB). Treatment may last, for example, for 1 week to 18 months or longer. The anti-therapeutic agent may be administered, e.g., once per day, six times weekly, five times weekly, four times weekly, three times weekly, two times weekly, or weekly.

In some embodiments, one or more anti-TB therapeutic agents may be administered as part of a DOTS (directly observed treatment, short-course) regimen or DOTS-Plus regimen (see, e.g., Guidelines for the programmatic management of drug-resistant tuberculosis, Geneva, World Health Organization. WHO/HTM/TB/2011.6 (2011) and Implementing the WHO Stop TB Strategy: a handbook for national tuberculosis control programmes. Geneva, World Health Organization. WHO/HTM/TB/2008.401 (2008), which are incorporated herein by reference).

Additionally, the methods and devices of the invention may be used for prognostic purposes, such as monitoring responsiveness to an anti-TB therapeutic agent and/or the need of further anti-TB therapeutic agent. Accordingly, in some embodiments, methods of the invention comprise:

(a) administering an anti-TB therapeutic agent to a subject with TB;

(b) measuring levels, e.g., protein levels, of three or more biomarkers in a biological sample from the subject, wherein the biomarkers are selected from
 (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"); and/or
 (ii) a second group consisting of A2Macro, MMP-2, VCAM-1, IL-17, and SCF ("Group II biomarker"); and (c)
 (i) identifying a subject as in need of further anti-TB therapeutic agent treatment if Group I biomarker levels are elevated in the biological sample compared to the control levels and/or if Group II biomarker levels are reduced in the biological sample compared to the control levels; or
 (ii) identifying a subject as in need of no further anti-TB therapeutic agent treatment if Group I biomarker levels are reduced or the same in the biological sample compared to the control levels and/or Group II biomarker levels are elevated or the same in the biological sample compared to the control levels.

In some embodiments, the method further comprises administering the anti-TB therapeutic agent to the subject identified as in need of further anti-TB therapeutic agent treatment. In some embodiments, the method further comprises cessation of administration of the anti-TB therapeutic agent to the subject identified as in need of no further anti-TB therapeutic agent treatment.

It is to be understood that the measuring step of the prognostic method can occur at any time during or after an anti-TB treatment regimen. For example, the measuring step may occur while the subject is still receiving treatment, such as an anti-TB therapeutic agent, or after treatment has stopped, for example 1, 2, 3, 4, 5, 6, or 7 days, or 1, 2, 3, 4, 5, 6 or more weeks after treatment has stopped. Thus, the prognostic method is useful for determining whether a subject should continue treatment if the subject is already receiving treatment, or whether a subject should be given further treatment if the subject has stopped receiving treatment.

It is to be understood that a subset of biomarkers described herein may be used in any of the methods provided herein including, e.g., the biomarker subset IL-1RA, IL-8, IL-18, VEGF, and IL-6 or the biomarker subset IL-8, IL-18, VEGF, and IL-6.

Detection Methods

The methods and devices of the invention may be protein or mRNA based. Examples of protein-based assays include immunoassays (also referred to herein as immune-based assays), Western blots, Western immunoblotting, multiplex bead-based assays, and assays involving aptamers (such as SOMAmer™ technology) and related affinity agents. Examples of mRNA-based assays include Northern analysis, quantitative RT-PCR, microarray hybridization, and multiplex bead-based assays. These assays generally and commonly detect and measure the level of the biomarker of interest. The level of the biomarker may then be compared to a control level. Control levels will be discussed in greater detail herein.

Protein Detection

The art is familiar with various methods for analyzing protein levels. An exemplary immunoassay may be carried out as follows: A biological sample is applied to a substrate having bound to its surface biomarker-specific binding partners (i.e., immobilized biomarker-specific binding partners). The biomarker-specific binding partner (which may be referred to as a "capture ligand" because it functions to capture and immobilize the biomarker on the substrate) may be antibodies or antigen-binding antibody fragments such as Fab, F(ab)2, Fv, single chain antibodies, Fab and sFab fragments, F(ab')2, Fd fragments, scFv, and dAb fragments, although they are not so limited. Other binding partners are described herein. Biomarkers present in the biological sample bind to the capture ligands, and the substrate is washed to remove unbound material. The substrate is then exposed to soluble biomarker-specific binding partners (which may be identical to the binding partners used to immobilize the biomarker). The soluble biomarker-specific binding partners are allowed to bind to their respective biomarkers immobilized on the substrate, and then unbound material is washed away. The substrate is then exposed to a detectable binding partner of the soluble biomarker-specific binding partner. In one embodiment, the soluble biomarker-specific binding partner is an antibody having some or all of its Fc domain. Its detectable binding partner may be an anti-Fc domain antibody. As will be appreciated by those in the art, if more than one biomarker is being detected, the assay may be configured so that the soluble biomarker-specific binding partners are all antibodies of the same isotype. In this way, a single detectable binding partner, such as an antibody specific for the common isotype, may be used to bind to all of the soluble biomarker-specific binding partners bound to the substrate.

It is to be understood that the substrate may comprise capture ligands for one or more biomarkers, including two or more, three or more, four or more, five or more, etc. up to and including all twenty of the biomarkers provided by the invention.

In some instances, it may be preferable to measure biomarkers having the lowest detectable concentration. An example would be biomarkers having protein concentrations in the pg/ml range. In blood samples taken from TB-positive and TB-negative subjects, biomarkers in the pg/ml include IL-18, IL-1RA, IL-6, IL-8, TNF-alpha and VEGF (Group I biomarkers) and IL-17 and SCF (Group II markers). Accordingly, in some assays contemplated by the invention, protein levels of two, three, four, five or more of these biomarkers may be measured on the same substrate. As a further example, the substrate may comprise capture ligands for two, three, four or all five of the following Group I biomarkers: IL-18, IL-1RA, IL-6, IL-8, and VEGF. As a further example, the substrate may comprise capture ligands for two, three, or all four of the following Group I biomarkers: IL-18, IL-6, IL-8, and VEGF.

In some instances, it may be preferable to measure, on a single substrate, biomarkers having protein concentrations that are in the same dynamic range (i.e., they are present in the biological sample in the same concentration range). The biomarkers may all be in the mg/ml or µg/ml range (e.g., Group I biomarkers: AAT, Fibrinogen, Haptoglobin, C3, beta-2-macroglobulin and CRP; and Group II biomarker: A2Macro), or they may all be in the ng/ml range (e.g., Group I biomarkers: ICAM-1, TIMP-1, and TNFR2; and Group II biomarkers: MMP-2 and VCAM-1), or they may all be in the pg/ml range (e.g., Group I biomarkers: IL-18, IL-1RA, IL-6, IL-8, TNF-alpha, and VEGF; and Group II markers: IL-17 and SCF). Those of ordinary skill in the art will be able to devise multiplexing assays (i.e., assays that measure two or more markers) using the guidance provided herein and the knowledge in the art.

In some embodiments, the invention contemplates a substrate having a pre-determined amount of capture ligands for each biomarker. The pre-determined amount of capture ligand is may be based in part on prior measurements of biomarker levels in subjects that are TB-positive and TB-negative. The assays may be designed such that if the subject is TB-positive, then one or more detectable signals appear, optionally on a biomarker-by-biomarker basis.

Other examples of protein detection methods include multiplexed immunoassays as described, e.g., in U.S. Pat. Nos. 6,939,720 and 8,148,171, and published US Patent Application No. 2008/0255766, and protein microarrays as described, e.g. in published US Patent Application No. 2009/0088329.

Protein Detection Binding Partners

Protein detection binding partners include biomarker-specific binding partners. In some embodiments, binding partners may be antibodies. As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and dAb fragments) as well as complete antibodies. Methods for making antibodies and antigen-binding fragments are well known in the art (see, e.g. Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Examples of commercially available biomarker-specific antibodies are shown in Table 3.

TABLE 3

Commercially Available Biomarker-Specific Antibodies

| Biomarker | Commercially Available Antibodies |
|---|---|
| IL-1RA | AS17 (BD Pharmingen), ab60978, ab2573, ab97301, ab104876, ab13776, ab123235 (abcam), 20D8 Mouse mAb #3865 (Cell Signaling Technology), IF1RN antibody (SDIX) |
| IL-6 | C3-4 and MQ2-6A3 (BD Pharmingen), ab6672, ab9324, ab11449 (abcam), MQ2-13A5, 6D9A1, 6C12B1, 5E1 (Novus Biologicals), AB1421 (EMD Millipore), IF6 antibody (SDIX) |
| IL-8 | G265-8 and G265-5 (BD Pharmingen), ab18672, ab7747, ab10769 (abcam), 6G4 (Sigma-Aldrich), 1G9 (Novus Biologicals), ABX-IF8 (Abgenix) |
| IL-18 | ab68435, ab117342, ab106939 (abcam), HPA003980 (Sigma-Aldrich), ABC8181 (Invitrogen) |
| VEGF | G153-694 and G143-850 (BD Pharmingen), ab46154, ab1316, ab68334, ab52917, ab14078, ab3109, ab28775, ab9570, ab16883, ab39250 (abcam), Bevacizumab, VEGF antibody (SDIX) |
| AAT | C3orf15 (Novus Biologicals), ab7635, ab9399, ab9400, ab7633 (abcam), 2B12 (Thermo Scientific), SAB4200198 (Sigma-Aldrich), SERPINA1 Antibody (SDIX) |
| CRP | Ab32412, ab31156, ab50861 (abcam), HPA027367 (Sigam-Aldrich) |
| Haptoglobin | Ab13429, ab8968, ab117316, ab131236, ab 97976 (abcam), 9G10 (Thermo Scientific), 2F4, 2B8, 6H2 (Novus Biologicals), HP Antibody (SDIX) |
| TNFR2 | Ab8161, ab15563, ab17038, ab16920, ab117543 (abcam), GWB-5DAFEF (GenWay Biotech, Inc.) |
| B2M | PA5-12361, B2M-01 (Thermo Scientific), NB500-317 (Novus Biologicals), ab759, ab15976 (abcam), B2M Antibody (SDIX) |
| TIMP-1 | EP1549RY, MM0034-4A16, SPM355 (Novus Biologicals), ab1827, ab38978, ab61224, ab2464 (abcam) |
| Fibrinogen | 27C8 (Novus Biologicals), ab34269, ab6666, ab118488, ab118810 (abcam), |
| ICAM-1 | EPR4776, MEM-111, 1H4 (Novus Biologicals), ab2213, ab7815, ab20, ab53013 (abcam), 4915 (Cell Signaling Technology), enlimomab, |
| C3 | 11H9, 474 (Novus Biologicals), 11H9 (Thermo Scienitfic), ab97462, ab14232, ab36989 (abcam) |
| TNF-alpha | MAB11, T1 (Novus Biologicals), ab1793, ab6671, ab9739, ab66579 (abcam), TNF Antibody (SDIX) |
| A2Macro | EPR4432, NB120-8770, NBP1 -85491 (Novus Biologicals), ab58703, ab36995, ab7337, ab48555 (abcam) |
| MMP-2 | NB200-193, 8B4, 2C1 (Novus Biologicals), ab80737, ab3158, ab37150, ab2462 (abcam) |
| VCAM-1 | 6G9, EPR5047 (Novus Biologicals), ab98954, ab106777,ab95139 (abcam), VCAM1 Antibody (SDIX), |
| IL-17 | EP434Y, P3814, NBP1-76337 (Novus Biologicals), ab79056, ab77171 (abcam) |
| SCF | EP665Y, NBP1-77030, NBP1-59192 (Novus Biologicals), ab9716, ab64677, ab72325 (abcam) |

Binding partners also include proteins or peptides that bind to or interact with a target biomarker, e.g. through non-covalent bonding. For example, if the biomarker is a ligand, a binding partner may be a receptor for that ligand. In another example, if the biomarker is a receptor, a binding partner may be a ligand for that receptor. In yet another example, a binding partner may be a protein or peptide known to interact with a biomarker. Methods for producing proteins are well known in the art (see, e.g. Sambrook et al, "Molecular Cloning: A Laboratory Manual" (2nd Ed.), Cold Spring Harbor Laboratory Press (1989) and Lewin, "Genes IV", Oxford University Press, New York, (1990)) and can be used to produce binding partners such as ligands or receptors. Examples of proteins that interact with a target biomarker are shown in Table 4.

TABLE 4

Biomarker-Specific Protein-based Binding Partners

| Biomarker | Proteins that interact with biomarker |
|---|---|
| IL-1RA | IL1 receptor (Entrez ID 3554) |
| IL-6 | IL-6 receptor (Entrez ID 3570) |
| IL-8 | CXCR1 (Entrez ID 3577), CXCR2 (Entrez ID 3579) |
| IL-18 | IL-18 receptor (Entrez ID 8809), IL-18 binding protein (Entrez ID 10068) |
| VEGF | VEGF receptor I (Entrez ID 2321), VEGF receptor II (Entrez ID 3791) |
| AAT | CD16b (Entrez ID 2215) |
| Haptoglobin | Hemoglobin beta (Entrez ID 3043), Hemoglobin alpha 2 (Entrez ID 3040), Apolipoprotein A1 (Entrez ID 335) |
| TNFR2 | c-IAP1 (Entrez ID 329) and C-IAP2 (Entrez ID 330) |
| B2M | MHC class I alpha chain (Entrez ID 3133), CD1 (Entrez ID 909) |
| TIMP-1 | CD63 (Entrez ID 967) |
| Fibrinogen | CD44 (Entrez ID 960) |
| ICAM-1 | Integrin beta 2 (Entrez ID 3689), Filamin B (Entrez ID 2317) |
| TNF-alpha | TNF-Receptor 1 (Entrez ID 7132) and TNR-receptor 2 (Entrez ID 7133) |
| A2Macro | Surfactant Protein D (Entrez ID 6441) |
| MMP-2 | Integrin beta 3 (Entrez ID 3690) |
| VCAM-1 | SPARC (Entrez ID 6678), Integrin beta1 (Entrez ID 3688) |
| IL-17 | IL-17 receptor A (Entrez ID 23765), IL-17 receptor B (Entrez ID 55540), IL-17 receptor C (Entrez ID 84818), IL-17 receptor D (Entrez ID 54756), IL-17 receptor E (Entrez ID 132014) |
| SCF | c-KIT receptor (Entrez ID 3815) |

Binding partners also include aptamers and other related affinity agents. Aptamers include oligonucleic acid or peptide molecules that bind to a specific target molecule. Methods for producing aptamers to a target molecule are well known in the art (see, e.g., published US Patent Application No. 2009/0075834, U.S. Pat. Nos. 7,435,542, 7,807,351, and 7,239,742). Other examples of affinity agents include SOMAmer™ (Slow Off-rate Modified Aptamer, SomaLogic, Boulder, Colo.) modified nucleic acid-based protein binding reagents.

Binding partners also include any molecule capable of demonstrating selective binding to any one of the protein targets disclosed herein, e.g., peptoids (see, e.g., Reyna J Simon et al., "Peptoids: a modular approach to drug discovery" Proceedings of the National Academy of Sciences USA, (1992), 89(20), 9367-9371; U.S. Pat. No. 5,811,387; and M. Muralidhar Reddy et al., Identification of candidate IgG biomarkers for Alzheimer's disease via combinatorial library screening. Cell 144, 132-142, Jan. 7, 2011).

mRNA Detection

The art is familiar with various methods for analyzing mRNA levels. An exemplary quantitative RT-PCR assay may be carried out as follows: mRNA is extracted from cells in a biological sample (e.g., blood) using the RNeasy kit (Qiagen). Total mRNA is used for subsequent reverse transcription using the SuperScript III First-Strand Synthesis SuperMix (Invitrogen) or the SuperScript VILO cDNA synthesis kit (Invitrogen). 5 µl of the RT reaction is used for quantitative PCR using SYBR Green PCR Master Mix and gene-specific primers, in triplicate, using an ABI 7300 Real Time PCR System.

Expression profiles of cells in a biological sample (e.g., blood) can be carried out using an oligonucleotide microarray analysis. As an example, this analysis may be carried out using the custom designed oligonucleotide microarrays comprising oligonucleotides for all or a subset of the biomarkers described herein. The microarray may comprise 3 or more of the biomarkers, and may include Group I biomarkers only, or Group II biomarkers only, or a combination of Group I and Group II biomarkers. It is to be understood that such arrays may however also comprise positive and/or negative control markers such as housekeeping genes that can be used to determine if the array has been degraded and/or if the sample has been contaminated. The art is familiar with the construction of oligonucleotide arrays. See for example GeneChip Human Genome U133 Plus 2.0 Affymetrix expression array (Affymetrix). Other mRNA detection methods include multiplex detection assays well known in the art, e.g., xMAP® bead capture and detection (Luminex Corp., Austin, Tex.), and various oligonucleotide array assays (Illumina).

mRNA Detection Binding Partners mRNA detection binding partners include oligonucleotide or modified oligonucleotide (e.g. locked nucleic acid) probes that hybridize to a target mRNA. Probes may be designed using the GenBank Accession Nos. in Table 2. Methods for designing and producing oligonucleotide probes are well known in the art (see, e.g., U.S. Pat. No. 8,036,835; Rimour et al. GoArrays: highly dynamic and efficient microarray probe design. Bioinformatics (2005) 21 (7): 1094-1103; and Wernersson et al. Probe selection for DNA microarrays using OligoWiz. Nat Protoc. 2007; 2(11):2677-91).

Detectable Labels

Detectable binding partners may be directly or indirectly detectable. A directly detectable binding partner may be labeled with a detectable label such as a fluorophore. An indirectly detectable binding partner may be labeled with a moiety that acts upon (e.g., an enzyme or a catalytic domain) or is acted upon (e.g., a substrate) by another moiety in order to generate a detectable signal. These various methods and moieties for detectable labeling are known in the art.

Controls

In some embodiments, methods provided herein involve measuring a level of a biomarker in a biological sample and comparing the biomarker level to a control level in order to identify a subject having tuberculosis. The control level is a level of the same biomarker in a control tissue, control subject, or a population of control subjects.

The "control" may be (or may be derived from) a normal subject (or normal subjects). Normal subjects, as used herein, refer to subjects that are apparently healthy and show no TB-like symptoms. TB-like symptoms include a bad cough that lasts at least 2 weeks, chest pain, and coughing up blood or sputum. The control population may therefore be a population of normal subjects.

In other instances, the control may be (or may be derived from) an ill subject (or ill subjects) that presents with one or more TB-like symptoms. The Examples describe experiments in which the controls were "µl" subjects that presented with a cough that had lasted at least 2 weeks.

In still other instances, the control may be a biomarker level from a population of subjects regardless of whether they manifest or do not manifest TB-like symptoms (e.g., a subset of the general population).

In yet other instances, the control may be a subject or population of subjects from a specific geographic region, such as a continent or sub-continental region.

It is to be understood however that the methods provided herein do not require that a control level be measured every time a subject is tested. Rather, it is contemplated that control levels of biomarkers are obtained and recorded and that any test level is compared to such a pre-determined level. Such pre-determined control levels may also be referred to herein as pre-determined threshold levels which are discussed in greater detail herein.

Pre-Determined Thresholds

A pre-determined threshold describes a measurement value for a biomarker that aids in identifying a subject with TB. The pre-determined threshold for "upregulated biomarkers" (AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF) is a minimum value and any measurement at or above this value indicates that a subject may have TB. The pre-determined threshold for "downregulated biomarkers" (A2Macro, MMP-2, VCAM-1, IL-17, and SCF) is a maximum value and any measurement at or below this value indicates that a subject may have TB.

The pre-determined threshold may be calculated from control levels of each biomarker as measured from a control subject or population of subjects. In some embodiments, the pre-determined threshold is determined such that a certain specificity and/or sensitivity is achieved. In one example, an algorithm is used to determine each pre-determined threshold such that a certain specificity and/or sensitivity is achieved, as will be discussed in greater detail herein.

In some embodiments, the predetermined threshold for each biomarker is: 7 pg/ml for IL-6, 2.5 mg/ml for AAT, 20 ug/ml for CRP, 8 ng/ml for IL-8, 250 pg/ml for VEGF, 1.5 mg/ml for Haptoglobin, 6 ng/ml for TNFR2, 1.4 ug/ml for B2M, 60 ng/ml for TIMP-1, 5 mg/ml for Fibrinogen, 60 ng/ml for ICAM-1, 0.7 mg/ml for C3, 2 pg/ml for TNF-alpha, 160 pg/ml for IL-18, and 40 pg/ml for IL-1RA, 3 pg/ml for IL-17, 750 ng/ml for MMP 2, 100 pg/ml for SCF, 0.6 mg/ml for A2Macro, and 450 ng/ml for VCAM-1. The thresholds may be set within a range of these absolute values, including for example within 1%, 2%, 3%, 4%, 5%, 10%, 15%, or 20% of these values.

The foregoing thresholds are exemplary and it is to be understood that one of ordinary skill in the art is able to determine a control level based on the teachings provided herein and thereby establish new thresholds that may be used in the methods provided herein.

Sensitivity and Specificity Based Measurements

Diagnostic methods and devices, often times, are designed to achieve maximum specificity and sensitivity. Sensitivity and specificity, as used herein, are statistical measures of the performance of a diagnostic test that reads out either a TB-positive or a TB-negative status of a subject (i.e., a binary readout). Sensitivity is an indicator of the proportion of actual positives what are correctly identified as positives. In the context of the invention, sensitivity indicates the proportion of TB-positive subjects who are actually identified as such by the methods provided herein. Specificity is an indicator of the proportion of negatives that are correctly identified as negatives. In the context of the invention, specificity indicates the proportion of TB-negative subjects that are identified as such by the methods provided herein. In some instances, an end user of a diagnostic assay wants to maximize both sensitivity and specificity. To this end, the thresholds described herein can be used to achieve maximum specificity and sensitivity.

However, the invention contemplates that, in some instances, a medical practitioner or medical technician or other end user may modulate such thresholds and thereby modulate the degree of specificity and/or sensitivity that is desired. In other words, the invention contemplates that, in some instances, it may be sufficient and/or desirable to perform the diagnostic methods using thresholds that do not yield optimal sensitivity and specificity yet still provide sufficient information including sufficient identification of TB-positive subjects. As an example, an end user may desire to identify all subjects that are TB-positive even if it some TB-negative subjects are also identified. In this way, the end user can be certain that the method has identified all of the TB-positives. Such a method would be considered to have high sensitivity (since it would identify all the TB-positive subjects) but low specificity (since it would also identify some of the TB-negative subjects). In other words, the end user may be willing to tolerate false positives (i.e., TB-negative subjects that are identified as being TB-positive) but not false negatives (TB-positive subjects that are identified as being TB-negative). Thus, the methods may be performed by setting threshold values that provide for a desired level of specificity without regard to sensitivity, or that provide for a desired level of sensitivity without regard to specificity. In still other embodiments, the threshold values may be adjusted to provide for sub-optimal levels of sensitivity and specificity. Typically, at a minimum, either the specificity or the sensitivity is set to greater than 50%. In some embodiments, thresholds are adjusted to provide for at least 60%, or at least 70%, or at least 80%, or at least 90%, or higher sensitivity and/or at least 60%, or at least 70%, or at least 80%, or at least 90%, or higher specificity.

Figure 5:
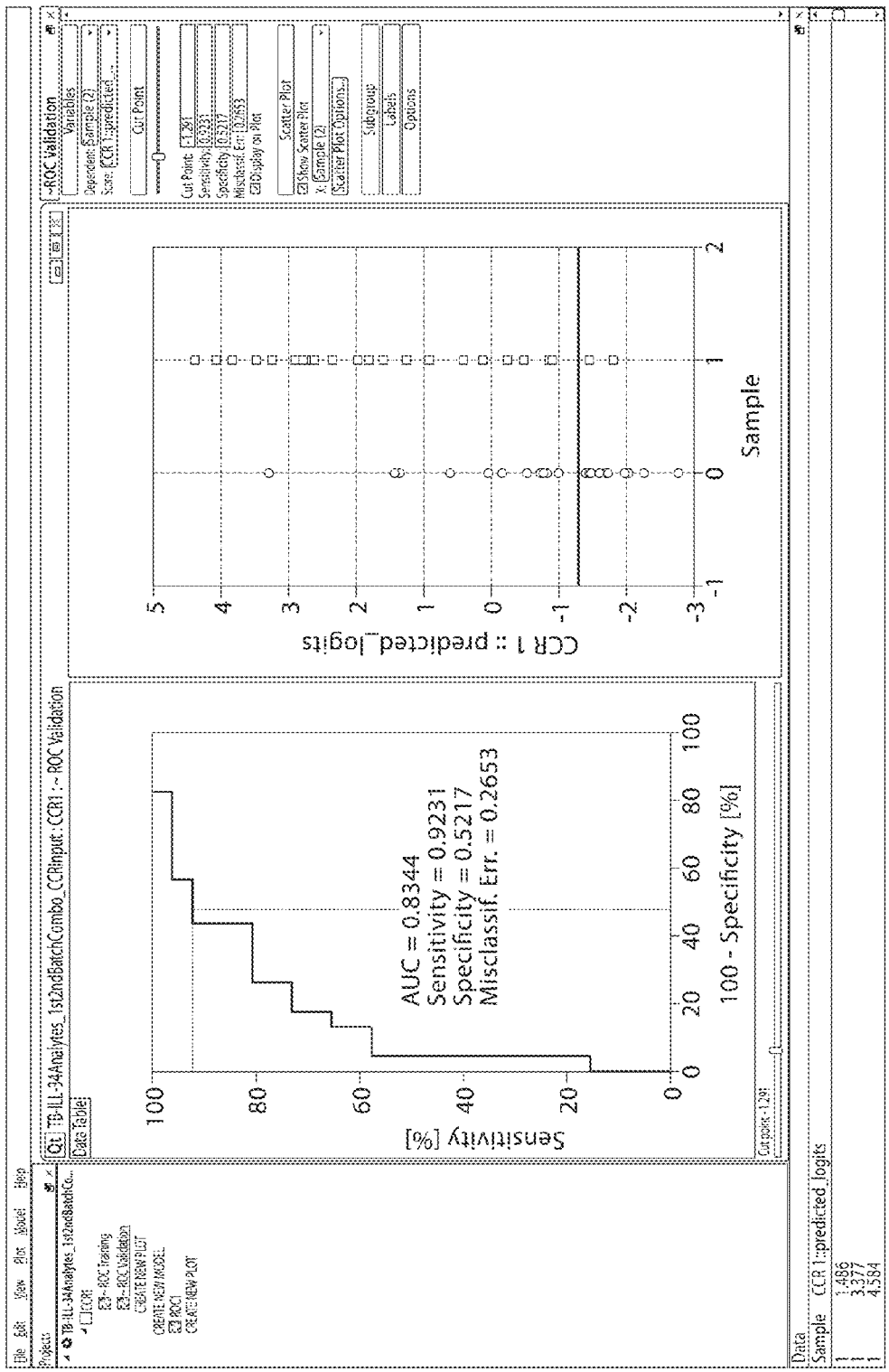
FIG. 5 is a screenshot of the COBExpress program and shows an ROC plot (left) and cutpoint values (right) for a biomarker panel consisting of IL-6, VEGF, IL-18, IL-8, and IL-1RA. Circles indicate control (ill) subjects. Squares indicate TB subjects.
Figure 6:
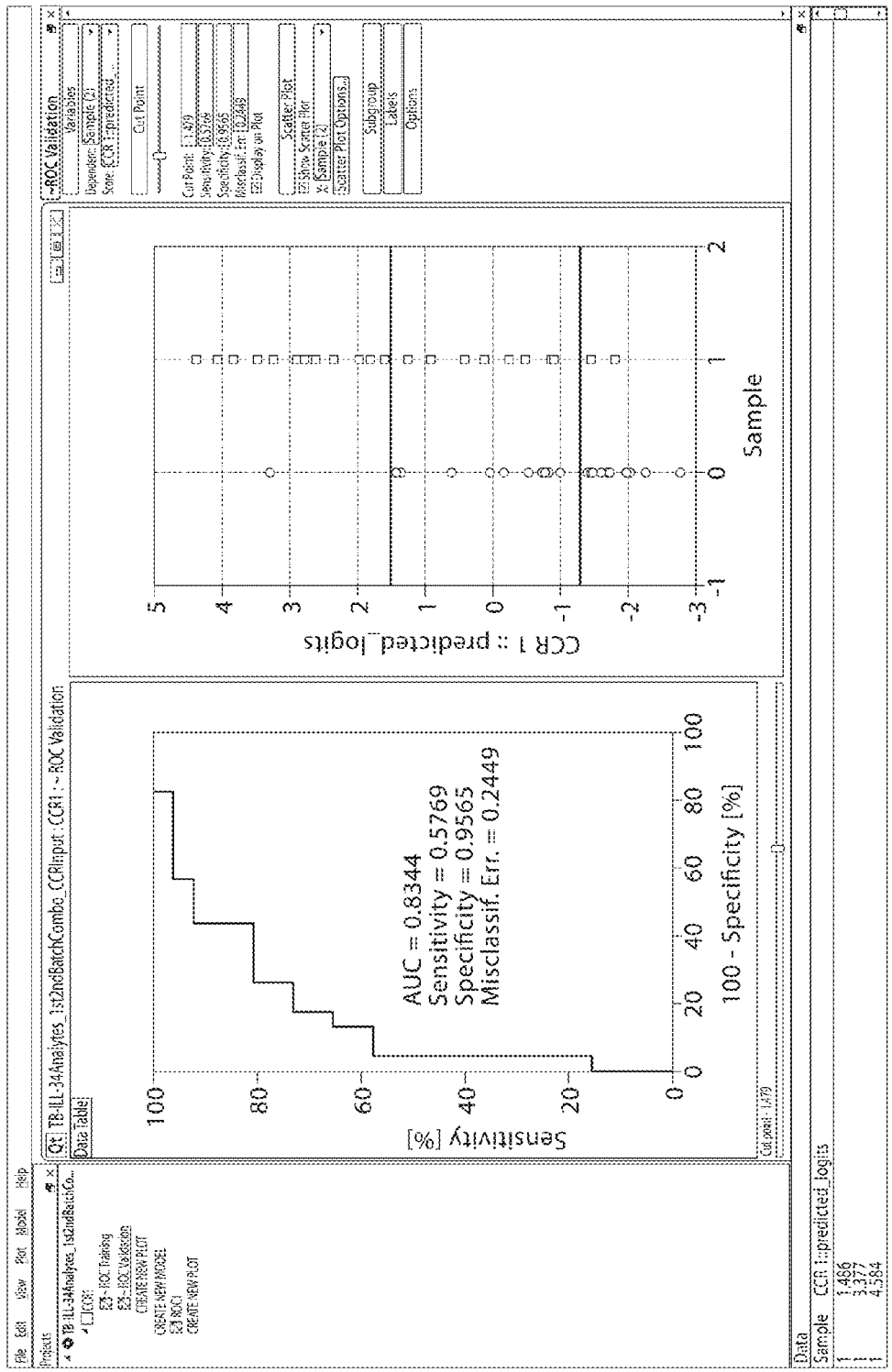
FIG. 6 is a screenshot of the COBExpress program and shows an ROC plot (left) and cutpoint values (right) for a biomarker panel consisting of IL-6, VEGF, IL-18, IL-8, and IL-1RA. Circles indicate control (ill) subjects. Squares indicate TB subjects.

FIG. 5 illustrates how thresholds may be chosen to achieve a desired level of specificity and/or sensitivity. The TB and ill controls are shown for a validation set taken randomly form 56 TB cases and 53 "ill" controls. In this example, 5 proteins in the pg/ml biomarker set are used together with a commercially available statistical software package called CORExpress for sample classification. The left hand pane shows the ROC plot specifying the final sensitivity and specificity values achieved by adjusting the cutpoint, the bold black line on the right hand pane. The cutpoint adjustment is equivalent to adjusting the thresholds of the 5 biomarkers until a desired sensitivity and specificity is reached. The individual protein thresholds are not shown in this Figure. In this example, a maximum sensitivity of 92% and specificity of 52% was achieved (from an initial requirement that specificity be greater than 50%). FIG. 6 provides an illustration of achieving maximum sensitivity. The maximum specificity for the same biomarker set (5 of the pg/ml proteins) was 96% and sensitivity was 58% (although it was minimally set at greater than 50%).

Thus, it is to be understood that the thresholds for each of the biomarkers may be adjusted in order to achieve customized specificity and/or sensitivity levels.

Samples

The methods provided herein measure (and thus analyze) biomarker levels in biological samples. Biological samples, as used herein, refer to samples taken or derived from a subject. These samples may be tissue samples or they may be fluid samples (e.g., bodily fluid). Examples of biological fluid samples are whole blood, plasma, serum, urine, sputum, phlegm, saliva, tears, and other bodily fluids. In important embodiments, the biological sample is a whole blood sample.

The invention contemplates that certain biological samples do not require any prior manipulation prior to (or in order to facilitate) the measurement of the biomarker levels. As an example, the invention contemplates that a whole blood sample can be subjected to the methods provided herein to determine biomarker levels without need for prior work up.

Subjects

A subject is preferably a human. A subject may be HIV-positive or HIV-negative, as determined by standard diagnostic tests, e.g. an ELISA test. A subject may be an adult or a child. An adult is defined as 16 years of age or older. A subject may present as having had a cough for at least two weeks (referred to herein as a persistent cough).

A subset of the subjects having a persistent cough will be those having active TB (or TB disease). Such subjects are contagious and thus should be identified, treated and/or segregated from the population in order to contain spread of the disease. Earlier stages of TB infection may not be contagious and/or associated with TB-like symptoms such as persistent cough, chest pain, and blood in the sputum.

Devices

The invention contemplates devices that can used to perform the diagnostic methods provided herein. The devices will be designed to measure the level of three or more biomarkers and optionally compare such levels with control levels. It is to be understood that the device may comprise binding partners for any combination of biomarkers described herein or that can be contemplated by one of ordinary skill in the art based on the teachings provided herein.

The device may also comprise binding partners for one or more control markers. The control markers may be positive control markers (e.g., to ensure the device has maintained its integrity) and/or negative control markers (e.g., to identify contamination). The nature of the control markers will depend in part on the nature of the biological sample. If the biological sample is a blood sample, then the positive control may be albumin.

The device may therefore comprise binding partners for 1-20, 2-20, 3-20, 4-20, 5-20, 6-20, 7-20, 8-20, 9-20, 10-20, 11-20, 12-20, 13-20, 14-20, 15-20, 16-20, 17-20, 18-20, 19-20 or 20 of the biomarkers recited herein. In some instances, these are the only biomarkers being tested, besides the control markers, and the device is considered to consist of or consist essentially of these biomarkers since no other biomarkers would typically be required to diagnose TB. The total number of biomarkers on the device therefore may be equal to or less than 30, 29, 28, 27, 26, 25, 24, 23, 22, 21, 20, 19, 18, 17, 16, 15, 14, 13, 12, 11, 10, 9, 8, 7, 6, 5, 4, or 3.

In some embodiments, the device may comprise binding partners for biomarkers within a particular dynamic range (e.g., the biomarkers are present in the biological sample in the same concentration range). For example, the device may comprise binding partners for biomarkers in the pg/mL range, the ng/mL range, and/or the µg/mL range. A pg/ml range means a detectable concentration range up to 1000 pg/ml. A ng/ml range means a detectable concentration range of 1-1000 ng/ml. A µg/ml range means a detectable concentration range of 1-1000 µg/ml. A mg/ml range means a detectable concentration range of 1-1000 mg/ml. In some instances, the dynamic range spans the µg/ml and mg/ml ranges.

Typically the devices will comprise a substrate to which are bound binding partners for the three or more biomarkers being measured. The binding partners may be antibodies, antigen-binding antibody fragments, receptors, ligands, aptamers, and the like, provided they bind selectively to the biomarker being tested and do not bind appreciably to any other biomarker that may be present in the biological sample loaded onto the device. The presence of the biomarker of interest (and thus its binding to its respective binding partner) may be indicated by any means including without limitation fluorescent, chemical, and electrical means.

The binding partners may be provided on the substrate in a predetermined spatial arrangement. A substrate, as used herein in this context, refers to a solid support to which biomarker-specific binding partners may be bound. The substrate may be paper or plastic (e.g., polystyrene) or some other material that is amenable to the biomarker measurement. The substrate may have a planar surface although it is not so limited. In some instances, the substrate is a bead or sphere.

The device may be a microfluidics device (e.g., a miniaturized device that handles volumes in the microliter range) which optionally may comprise microfluidics channels. The device may have one or more sample inlets where the biological sample is loaded onto the device (and typically also the substrate).

The device may transport sample and reagents (if necessary) to desired locations in the device or in the substrate using channels or simply by movement of a solution from the sample inlet to the region of biomarker-specific binding partners. In some embodiments, the sample and reagents may be transported by shaking of the device or by pumps.

The device may further comprise one or more reagents or one or more wash solutions necessary for operation of the device. The reagents may for example soluble binding partners for the biomarkers and/or labeled isotype-specific antibodies or antibody fragments. These reagents may be stored on the device and released only after the biological sample has been introduced and the biomarkers contained therein are allowed to bind to their respective binding partners. The wash solutions may be released as required. These reagents and/or wash solutions may be stored for example in blister packs on the device. Alternatively, they may be added to the device when needed.

The art is familiar with diagnostic devices and reference can be made to U.S. Pat. Nos. 7,897,356 and 7,323,143, and published US Patent Application Publication Nos. US 2008/0267999, US20120279298, PCT Publication Nos. WO/2012/151527, WO/2012/064704, and WO/2012/064878 and Martinez et al. PNAS, 2008, 105 (50): 19606-19611, all of which are incorporated herein by reference in their entirety.

EXAMPLES

Example 1: Determination of Biomarkers Associated with TB

Study Design

Collection and determination of TB subjects and control subjects is described in FIG. 1. Plasma samples and three sputum samples were collected from subjects with a cough lasting 2 or more weeks. Subjects were designated as having TB if their sputum samples had a positive result for a MTB (*Mycobacterium tuberculosis*) culture or both an AFB (acid-fast *bacillus*) smear and a MTB culture. Subjects were designated as an ill control if their sputum samples were negative for a MTB culture and negative for at least two or all three AFB smears. Subjects with a negative MTB culture and two or more positive AFB smears were designated as indeterminate and excluded from the study.

MTB culture involved culturing sputum obtained from a subject until the bacterial concentration reached a minimum value for identification. A BACTEC™ MGIT™ 960 System (BD, Franklin Lakes, N.J.) was used for MTB culture and detection. An acid-fast *bacillus* (AFB) smear was used to look for AFB, specifically MTB, in the sputum samples collected for each subject. For the smear, each sample was spread thinly onto a glass slide, treated with a special stain, and examined under a microscope. The HIV status of each subject was also determined using an ELISA test. HIV positive subjects were excluded from the analysis.

Study Cohort

After sputum sample analysis, 99 TB Case and 96 ill control subjects were identified and included in further analysis. Table 5 and Table 6 show the characteristics of the study cohort. The two groups were compared using the Mann-Whitney U test.

TABLE 5

Age Distribution of the Study Cohort

| Subject Group | Min | 1$^{st}$ Quarter | Median | Mean | 3$^{rd}$ Quarter | Max | P-value |
|---|---|---|---|---|---|---|---|
| ill | 17 | 27 | 30 | 34.92 | 40 | 79 | 0.796 |
| TB | 20 | 25 | 31.5 | 33.8 | 40.75 | 72 | |

TABLE 6

Mean Age, Number of Males and Females, and Mean Age of Males and Females in Study Cohort

| Subject Group | Mean Age | Standard Deviation | Number of Male | Number of Female |
|---|---|---|---|---|
| ill | 35 | 13 | 31 | 22 |
| TB | 34 | 11 | 34 | 22 |

| Subject Group | Male Mean Age | Male STDEV Age | Female Mean Age | Female STDEV Age |
|---|---|---|---|---|
| ill | 34 | 14 | 36 | 13 |
| TB | 37 | 11 | 29 | 8 |

Plasma Protein Profiling in Samples Using Myriad-RBM 100 microliters of plasma sample from subjects identified as a TB or control subject was analyzed for the presence and level of preselected proteins. Protein profiling of 109 (56 TB and 53 control) subjects was performed using the InflammationMap® v1.0 (Myriad-RBM, Austin, Tex.). The InflammationMap® is a 47-biomarker multi-analyte profile (MAP) designed to discern inflammatory biomarker patterns in a biological sample.

Data obtained from the InflammationMap® is summarized in FIG. 2 as boxplots for each biomarker in control (ill) and TB subjects. A box plot or boxplot (also known as a box-and-whisker diagram or plot) is a convenient way to graphically depict groups of numerical data through their five-number summaries: the smallest observation (sample minimum), lower quartile (Q1), median (Q2), upper quartile (Q3), and largest observation (sample maximum). A boxplot may also indicate which observations, if any, are considered outliers. The bottom and top of the box are always the 25th and 75th percentile (the lower and upper quartiles, respectively), and the band near the middle of the box is always the 50th percentile (the median). But the ends of the whiskers can represent several possible alternative values. In the boxplots of FIG. 2, these depict the minimum and maximum values excluding the outliers which are shown as dots beyond the whiskers. For example, for CRP ill Controls the minimum, maximum and median values are around 0, 80 and 205 ug/ml respectively. There is an outlier around 300 ug/ml.

Determination of TB-Associated Biomarkers

Figure 3:
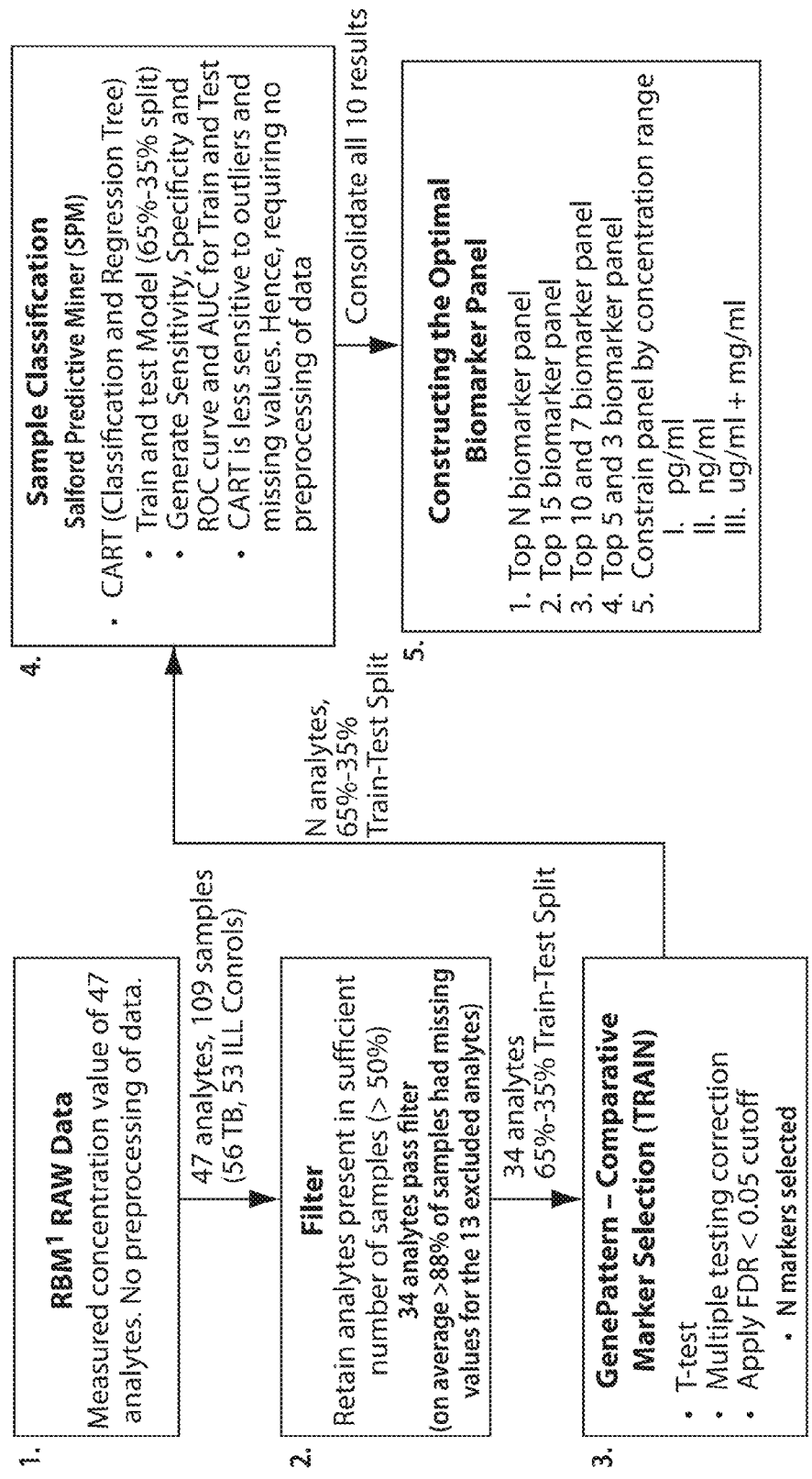
FIG. 3 is a flow chart depicting the data analysis process for determining biomarkers for use in identifying a subject with TB.
Figure 4A:
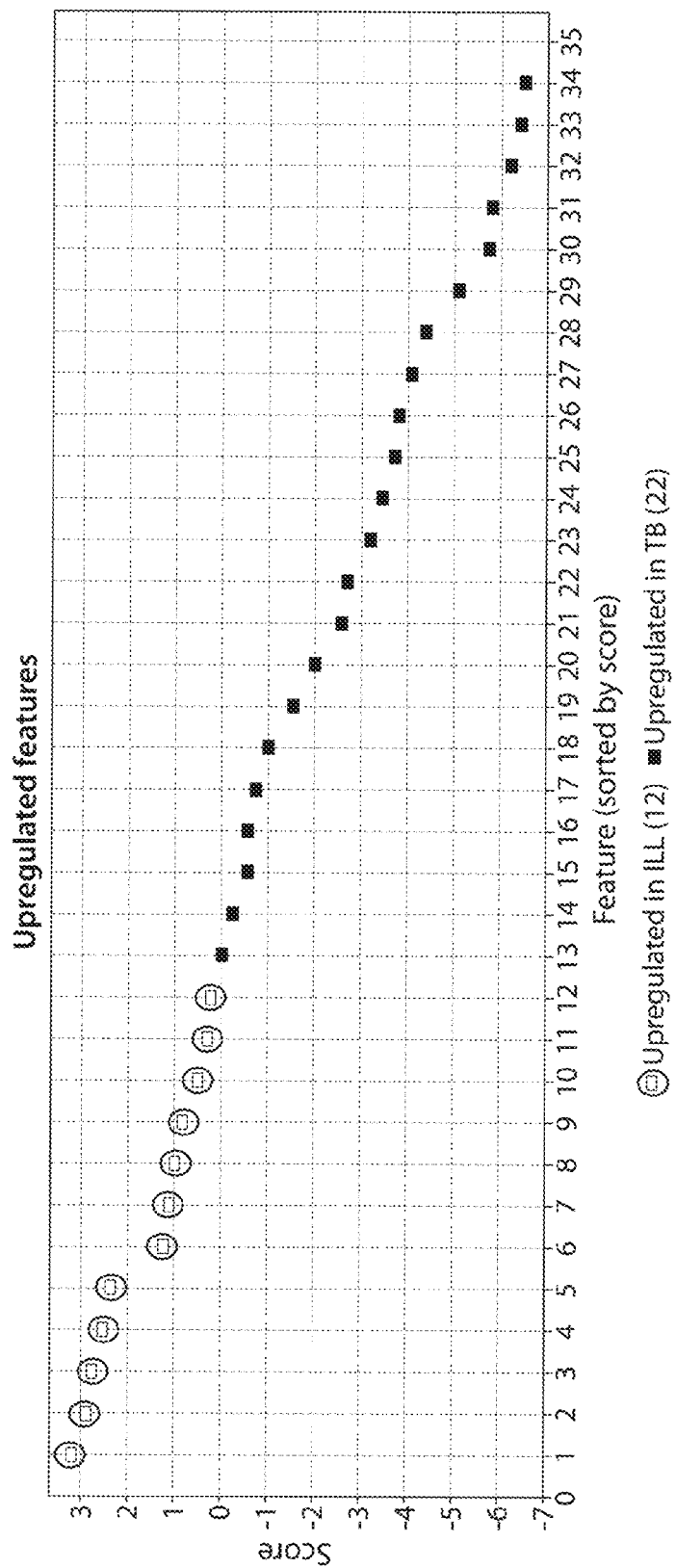
FIG. 4A is a graph depicting the biomarkers upregulated in TB or in control (ill) subjects.

The data obtained from protein profiling was run through data analysis as outlined in FIG. 3. Briefly, the raw data obtained from the InflammationMap® was filtered to remove biomarkers present in less than 50% of the samples. 34 biomarkers were found to be present in great than 50% of the samples and were further analyzed. Comparative Marker Selection of the biomarkers using GenePattern software (Broad Institute, Cambridge, Mass.) is shown in FIG. 4. False Discovery Rate (FDR) with multiple hypothesis correction was provided by the GenePattern module. A threshold of 0.05 or 5% was used to select differential markers.

15 biomarkers were found to be significantly up-regulated in subjects with TB compared to control subjects. These 15 biomarkers are: AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF. 5 biomarkers were found to be significantly down-regulated in control subjects compared to TB subjects. These 5 biomarkers are: A2Macro, MMP-2, VCAM-1, IL-17, and SCF.

Train-Test splits were performed with GenePattern software (Broad Institute, Cambridge, Mass.) and Salford Predictive Miner (Stanford, Palo Alto, Calif.) to produce example biomarker panels that identify a subject as having TB. For example, a 5 biomarker panel including IL-6, VEGF, IL-18, IL-8 and IL-1RA was found to produce a sensitivity of 90% and a specificity of 94% in the training set (39 TB subjects and 32 control subjects) and a sensitivity of 78% and a specificity of 91% in a validation test set (18 TB subjects and 21 control subjects taken randomly for the 56 TB subjects and 53 control subjects). In another example, a 10 biomarker panel including IL-6, VEGF, AAT, CRP, IL-1RA, TIMP-1, IL-8, IL-18, A2Macro, and Haptoglobin, was found to have a sensitivity of 90% and a specificity of 97% in the training set and a sensitivity of 78% and a specificity of 95% in the validation test set.

Example 2: Adjustment of Biomarker Thresholds to Attain Specified Sensitivity and Specificity COPExpress statistical software (Statistical Innovations, Belmont, Mass.) was used to adjust the threshold values of a 5 biomarker test set (IL-6, VEGF, IL-18, IL-8, and IL-1RA) to achieve a specified sensitivity and specificity. A Receiver Operating Characteristic (ROC) plot was generated with specificity and sensitivity values that were achievable for the biomarker set (Left panel, FIG. 5). The cutpoint (Right panel, bold line, FIG. 5) is a representation of the combined thresholds for the 5 biomarkers. As the cutpoint is increased or decreased, the specificity and sensitivity change. The cutpoint was adjusted to give a desired sensitivity and specificity. For example, in FIG. 5, the cutpoint chosen resulted in a sensitivity of 92% and a specificity of 52%. The cutpoint is then used to calculate the threshold values for the biomarkers. For example, a cutpoint that gives a specificity of 87% and sensitivity of 71% requires the following threshold levels for three biomarkers: IL-6: 7 pg/ml, VEGF: 250 pg/ml, and CRP: 20 ug/ml.

Example 3: Validation of IL-6, IL-8, IL-18, VEGF, and IL-1RA Biomarkers in Other TB Patient Populations Study Design Subjects were from the Dar (Dar es Salaam, Tanzania, "D", 179 samples), Pemba (Pemba Island, Tanzania, "P", 102 samples), or Bohol (Bohol, Philippines, "B", 100 samples) sites, providing a total of 381 samples.

Plasma samples and three sputum samples were collected from subjects with a cough lasting 2 or more weeks. Subjects were designated as having TB (being a TB case) if their sputum samples had a positive result for a MTB (*Mycobacterium tuberculosis*) culture or both an AFB (acid-fast *bacillus*) smear and a MTB culture. Subjects were designated as an ill control if their sputum samples were negative for a MTB culture and negative for at least two or all three AFB smears. Subjects with a negative MTB culture and two or more positive AFB smears were designated as indeterminate and excluded from the study.

MTB culture involved culturing sputum obtained from a subject until the bacterial concentration reached a minimum value for identification. A BACTEC™ MGIT™ 960 System (BD, Franklin Lakes, N.J.) was used for MTB culture and detection. An acid-fast *bacillus* (AFB) smear was used to look for AFB, specifically MTB, in the sputum samples collected for each subject. For the smear, each sample was spread thinly onto a glass slide, treated with a special stain, and examined under a microscope. The HIV status of each subject was also determined using an ELISA test. HIV positive subjects were excluded from the analysis.

Study Cohort

After sputum sample analysis, 194 TB Case and 187 ill control subjects were identified for the Dar (93 TB Case and 86 ill control), Pemba (51 TB Case and 51 ill control), and Bohol (50 TB Case and 50 ill control) sites and included in further analysis.

Plasma Protein Profiling in Samples Using Myriad-RBM

A 100 microliter plasma sample from subjects identified as a TB case or as an ill control was analyzed for the presence and level of preselected proteins. Protein profiling of 381 samples was performed using the Inflammation- Map® v1.0 (Myriad-RBM, Austin, Tex.). The InflammationMap® is a 47-biomarker multi-analyte profile (MAP) designed to discern inflammatory biomarker patterns in a biological sample. The data obtained from protein profiling was analyzed as outlined in FIG. 3.

Figure 7:
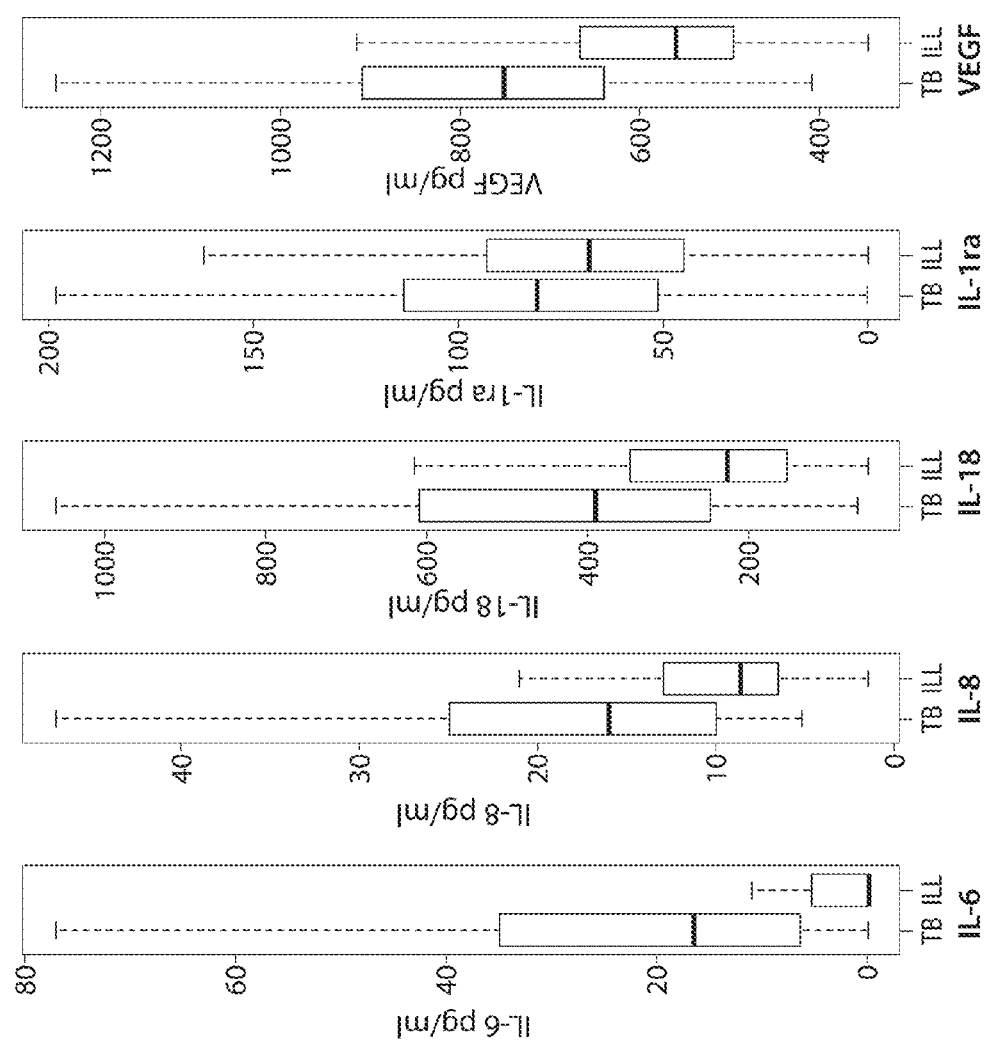
FIG. 7 is a series of box plots depicting the raw data obtained for IL-6, IL-8, IL-18, IL-1RA, and VEGF in TB subjects or control (ill) subjects in the expanded TB study including all 3 cohorts (Dar, Pemba, and Bohol). The Y-axis label is pg/mL for each box plot.
Figure 8:
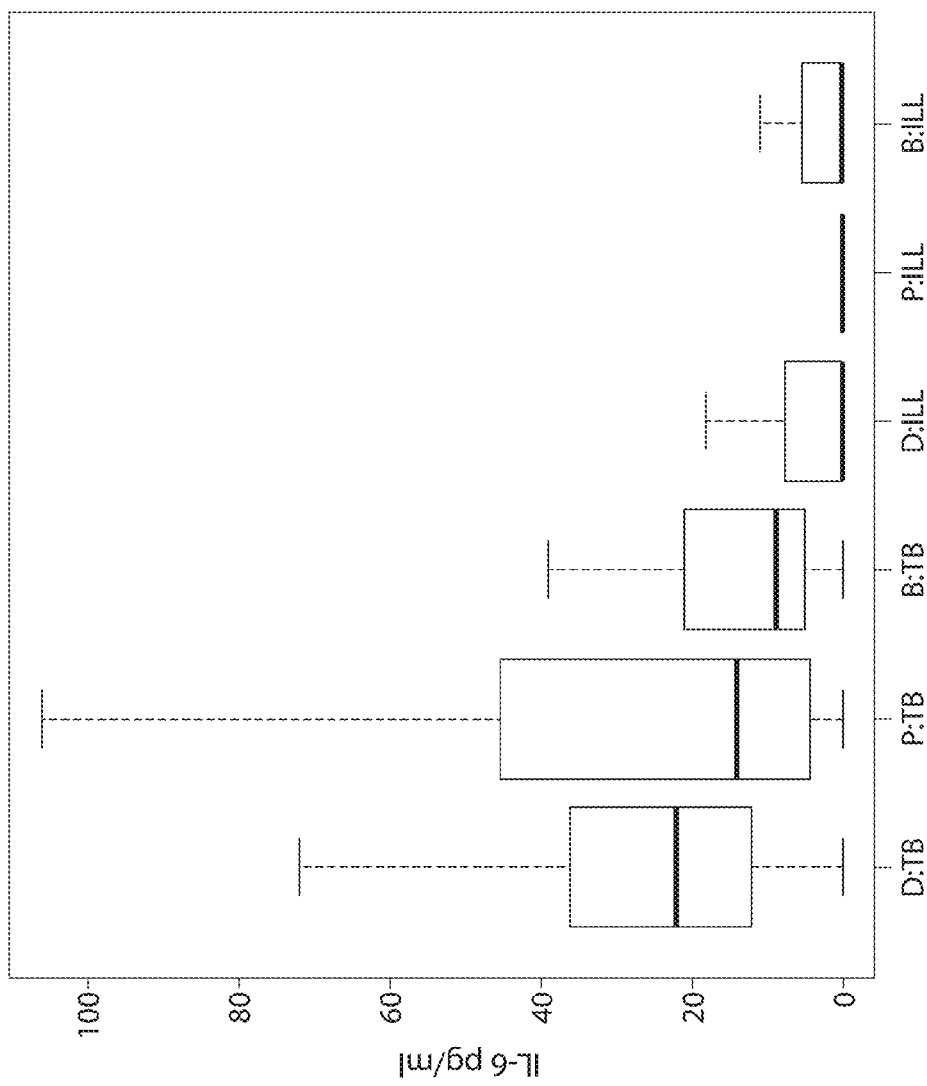
FIG. 8 is a series of box plots depicting the raw data obtained for IL-6 in TB subjects or control (ill) subjects in each cohort (Dar TB=D:TB, Dar ill=D: ill; Pemba TB=P: TB, Pemba ill=P: ill; Bohol TB=B:TB, Bohol ill=B: ill).
Figure 9:
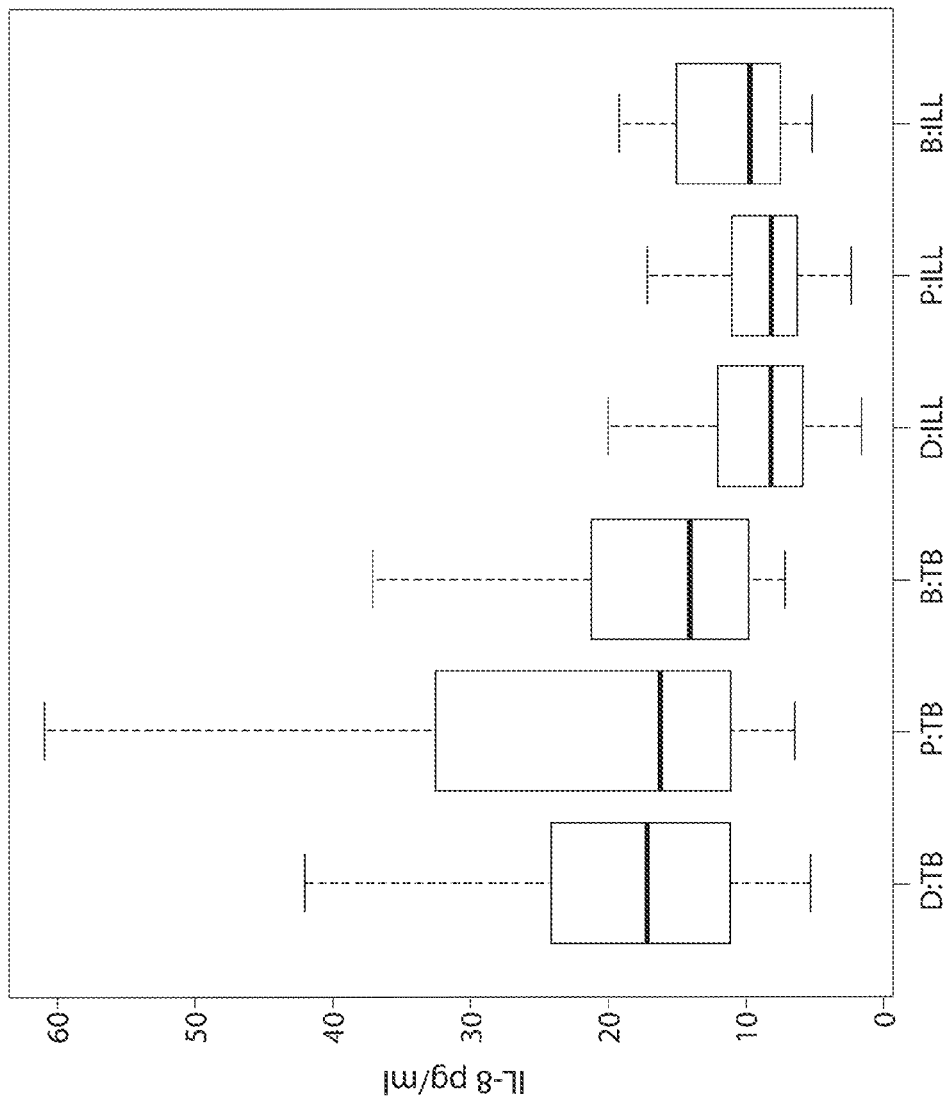
FIG. 9 is a series of box plots depicting the raw data obtained for IL-8 in TB subjects or control (ill) subjects in each cohort (Dar TB=D:TB, Dar ill=D: ill; Pemba TB=P: TB, Pemba ill=P: ill; Bohol TB=B:TB, Bohol ill=B: ill).
Figure 10:
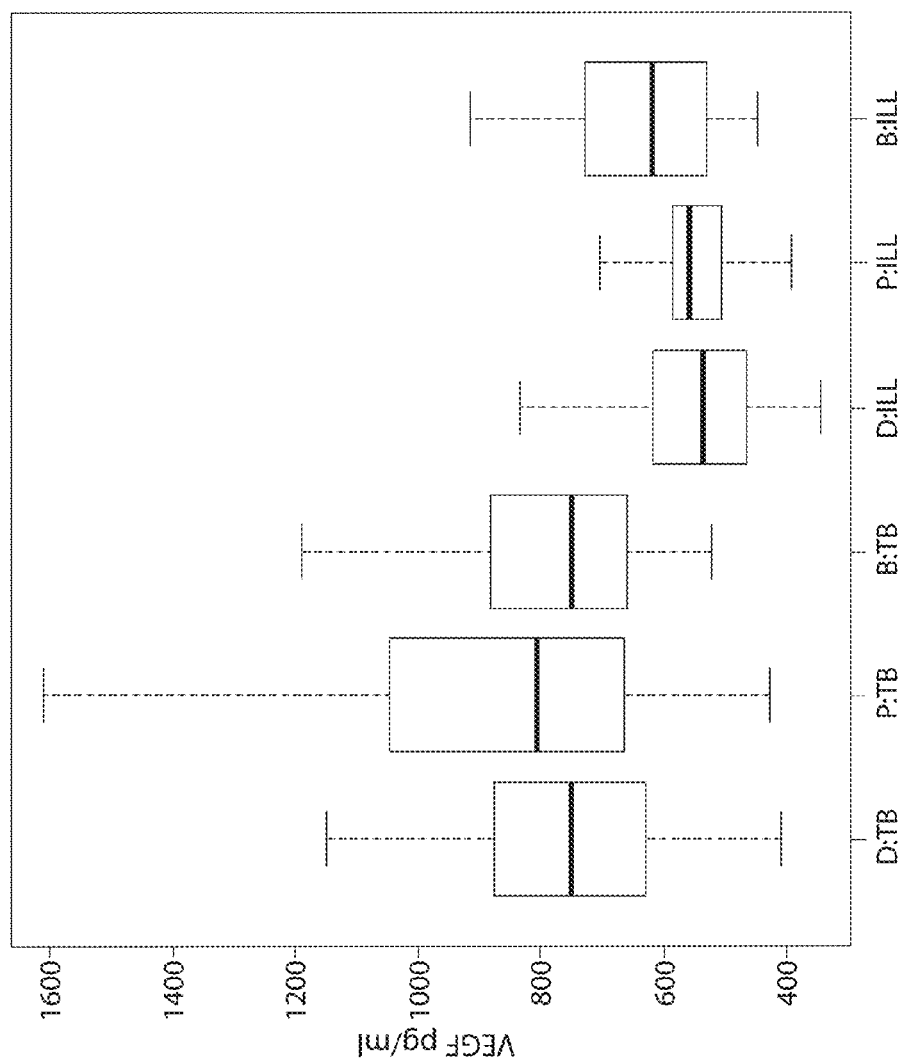
FIG. 10 is a series of box plots depicting the raw data obtained for VEGF in TB subjects or control (ill) subjects in each cohort (Dar TB=D:TB, Dar ill=D: ill; Pemba TB=P: TB, Pemba ill=P: ill; Bohol TB=B:TB, Bohol ill=B: ill).
Figure 11:
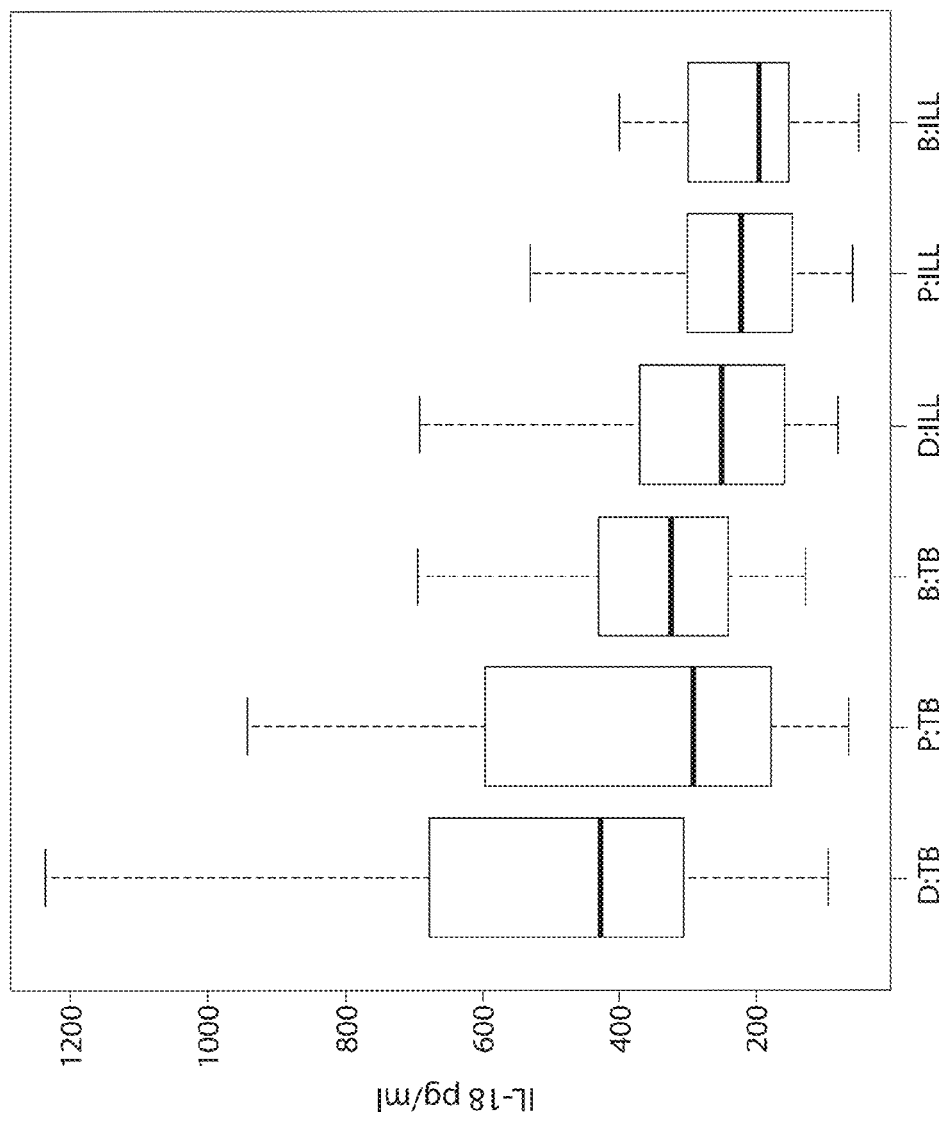
FIG. 11 is a series of box plots depicting the raw data obtained for IL-18 in TB subjects or control (ill) subjects in each cohort (Dar TB=D:TB, Dar ill=D: ill; Pemba TB=P: TB, Pemba ill=P: ill; Bohol TB=B:TB, Bohol ill=B: ill).
Figure 12:
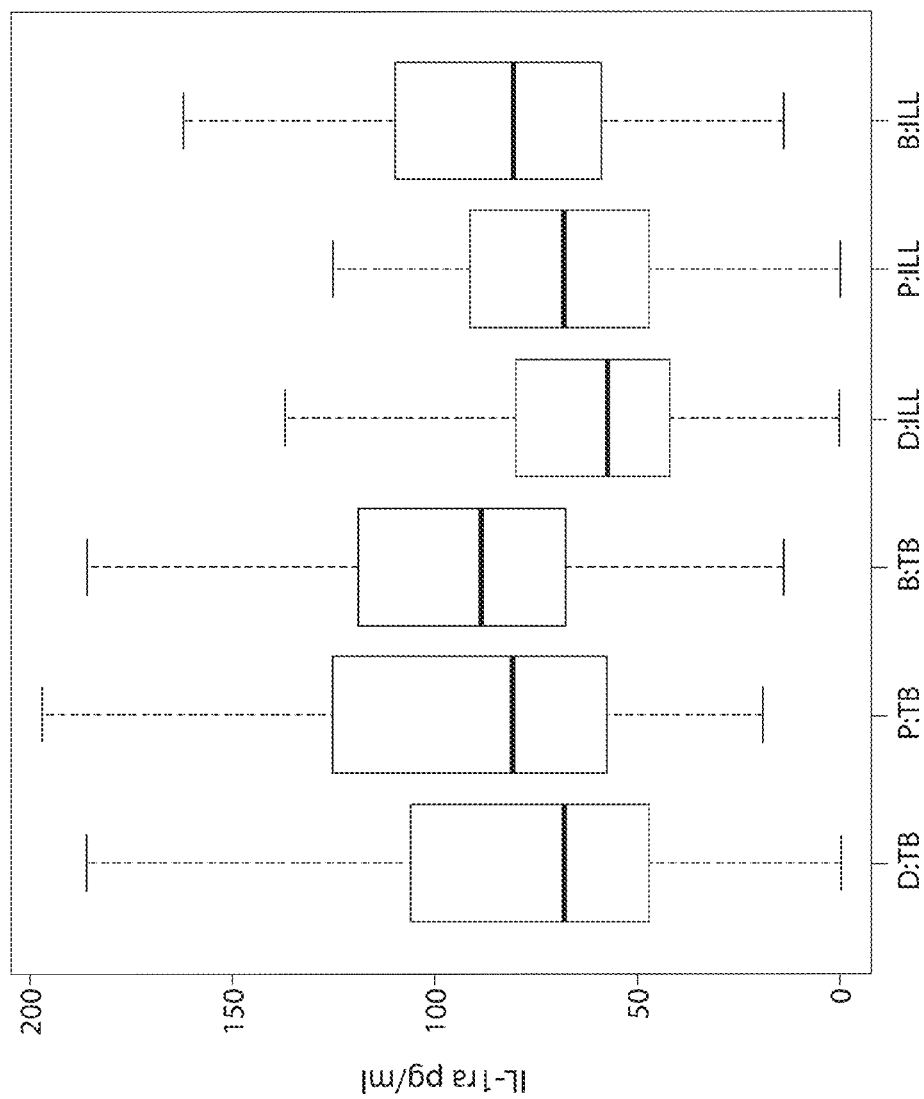
FIG. 12 is a series of box plots depicting the raw data obtained for IL-1RA in TB subjects or control (ill) subjects in each cohort (Dar TB=D:TB, Dar ill=D: ill; Pemba TB=P: TB, Pemba ill=P: ill; Bohol TB=B:TB, Bohol ill=B: ill).

Data obtained from the InflammationMap® is summarized in FIG. 7 for all 3 sites (Dar, Pemba, and Bohol) combined and in FIGS. 8-12 for each site individually as boxplots for each of IL-6, IL-8, IL-18, IL-1RA, and VEGF in control (ill) and TB case subjects. Further description of boxplots is provided in Example 1.

Validation of IL-6, IL-8, IL-18, VEGF, and IL-1RA Biomarkers Using Train/Test Splits Train/Test splits were performed with GenePattern software (Broad Institute, Cambridge, Mass.) and Salford Predictive Miner (Stanford, Palo Alto, Calif.). Validation was performed using different samples than the train/test set.

Figure 13:
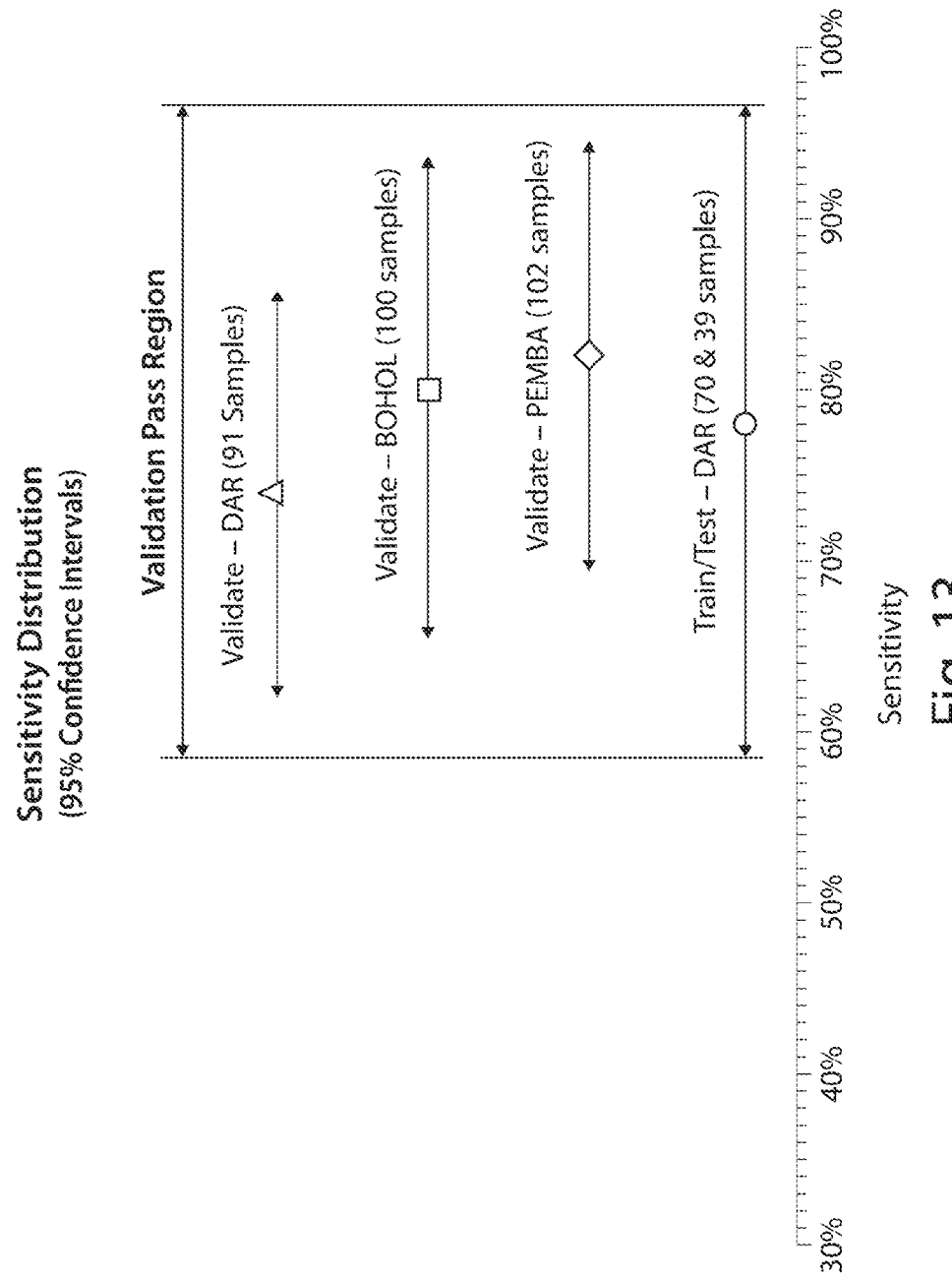
FIG. 13 is a plot of the sensitivity distribution for each cohort (Dar=D, Pemba=P, Bohol=B) using the train/test set from Example 1. The validation pass range is indicated by vertical lines.
Figure 14:
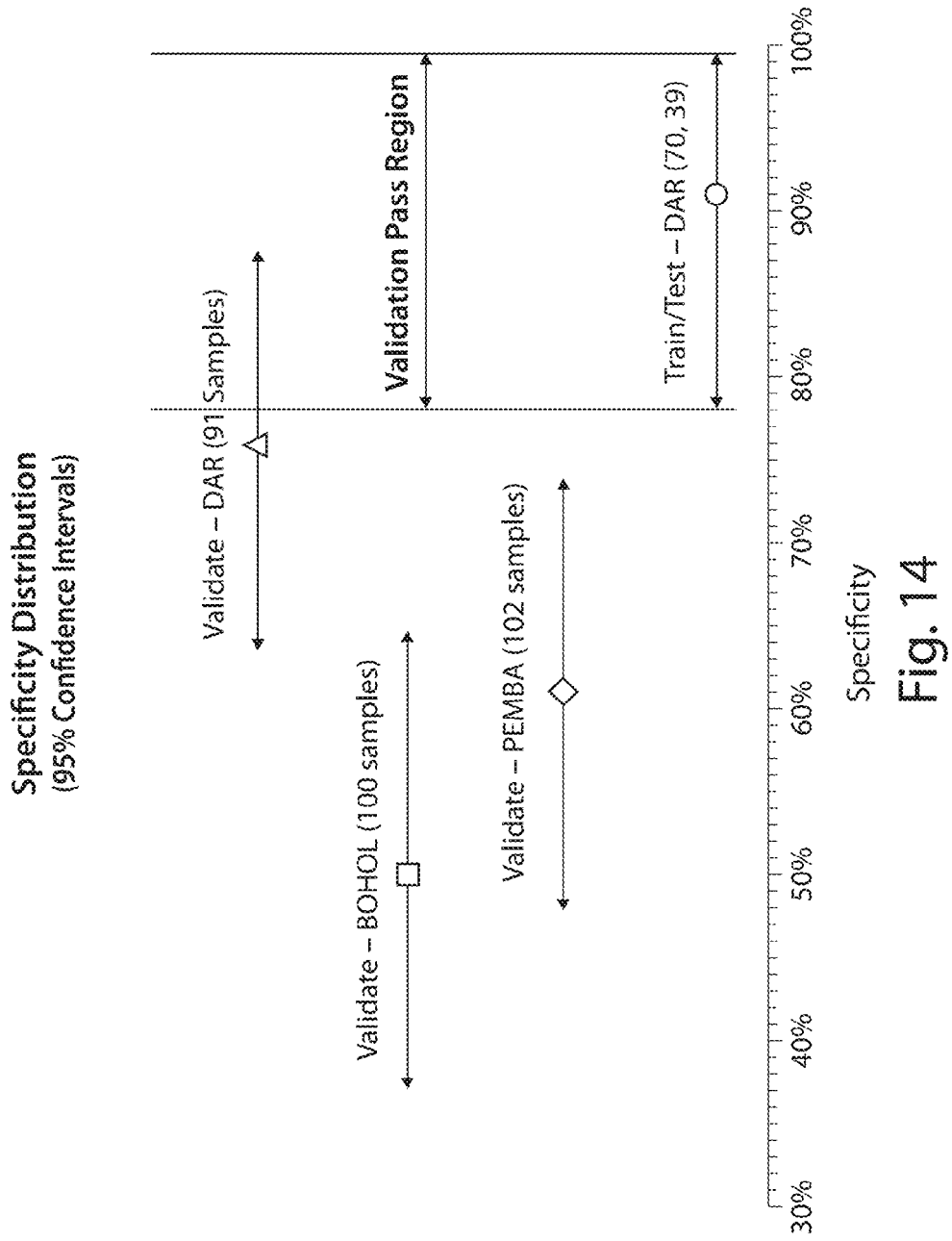
FIG. 14 is a plot of the specificity distribution for each cohort (Dar=D, Pemba=P, Bohol=B) using the train/test set from Example 1. The validation pass range is indicated by vertical lines.

First, validation of the Example 1 train/test set was performed using the 5 biomarker panel (IL-6, IL-8, IL-18, VEGF, and IL-1RA) for each separate site (DAR, BOHOL, and PEMBA). FIG. 13 shows that the sensitivity measurements using the 5 biomarker panel passed validation for all three sites. FIG. 14 shows that the specificity measurements using the 5 biomarker panel passed validation for the DAR site.

Further validation using global analysis was undertaken using 12 different train/test samples and validation samples (Table 7). The numbers next to each train/test sample correspond to the numbers in FIGS. 15 and 16.

TABLE 7

Train/test samples and validation samples

| Train/Test Samples | Validation Samples |
|---|---|
| 1. DAR, PEMBA, BOHOL | DAR, PEMBA, BOHOL (5 biomarkers, IL-6, IL-8, IL-18, VEGF, and IL-1RA) |
| 2. DAR, PEMBA, BOHOL | DAR, PEMBA, BOHOL (4 biomarkers, IL-6, IL-8, IL-18, and VEGF) |
| 3. DAR, PEMBA, BOHOL | DAR, PEMBA, BOHOL (3 biomarkers, IL-6, IL-8, and IL-18) |

TABLE 7-continued

Train/test samples and validation samples

| Train/Test Samples | Validation Samples |
|---|---|
| 4. DAR | PEMBA (5 biomarkers, IL-6, IL-8, IL-18, VEGF, and IL-1RA) |
| 5. DAR | BOHOL (5 biomarkers, IL-6, IL-8, IL-18, VEGF, and IL-1RA) |
| 6. PEMBA | DAR (5 biomarkers, IL-6, IL-8, IL-18, VEGF, and IL-1RA) |
| 7. PEMBA | BOHOL (5 biomarkers, IL-6, IL-8, IL-18, VEGF, and IL-1RA) |
| 8. DAR (Pilot Study) | PEMBA (102 samples) |
| 9. DAR (Pilot Study) | BOHOL (100 samples) |
| 10. DAR (Pilot Study) | DAR (91 samples) |
| 11. DAR (Pilot Study) | DAR (51 samples/Pilot) |
| 12. DAR (Pilot Study) | DAR (51 samples/Validation) |

Figure 15:
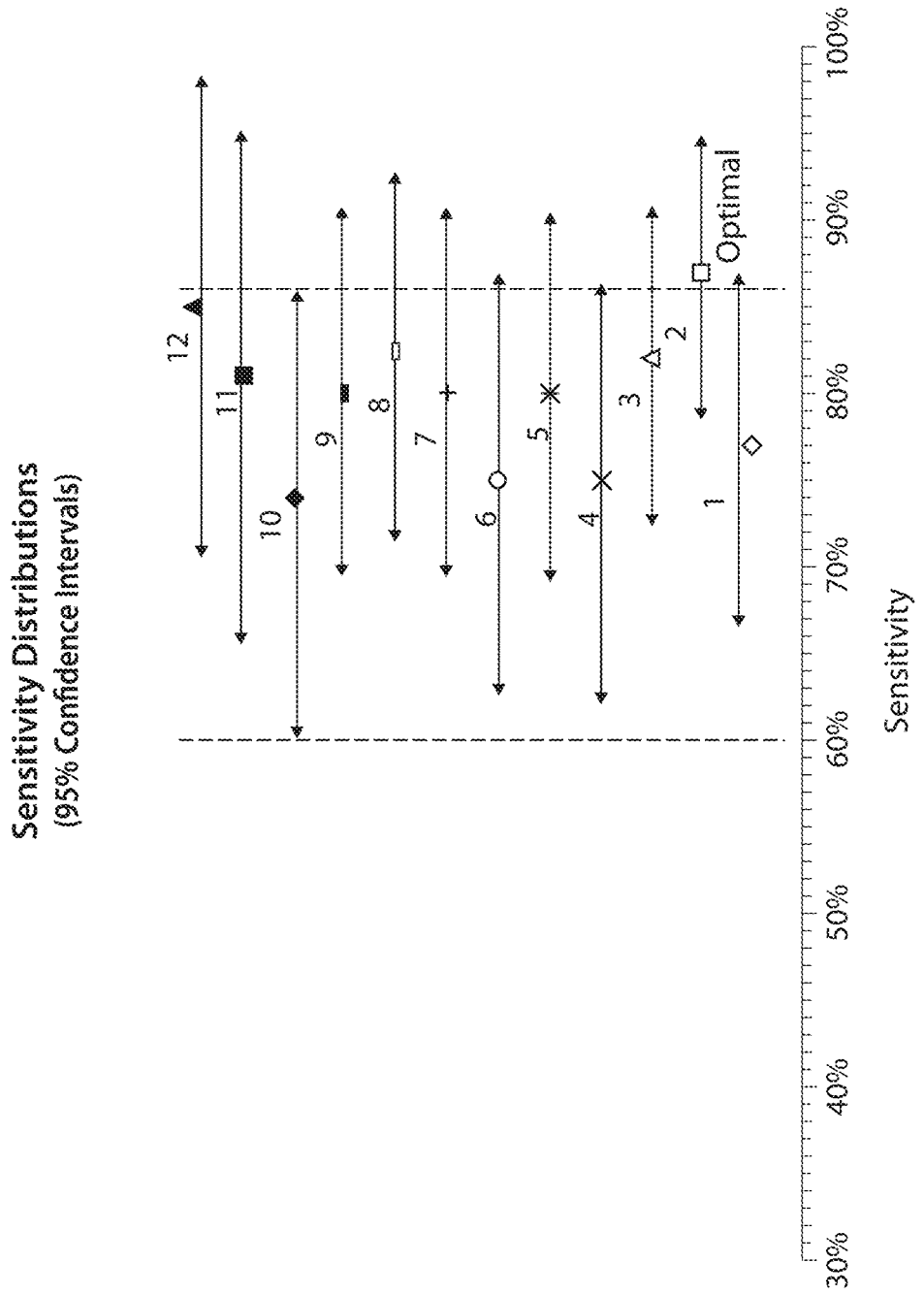
FIG. 15 is a plot of the sensitivity distributions for each validation test set as defined in Table 8 (i.e., the number above each double-headed arrow line corresponds to the validation test set with the same number in Table 8, the numbers are listed from 12 to 1 from top to bottom above each arrow).
Figure 16:
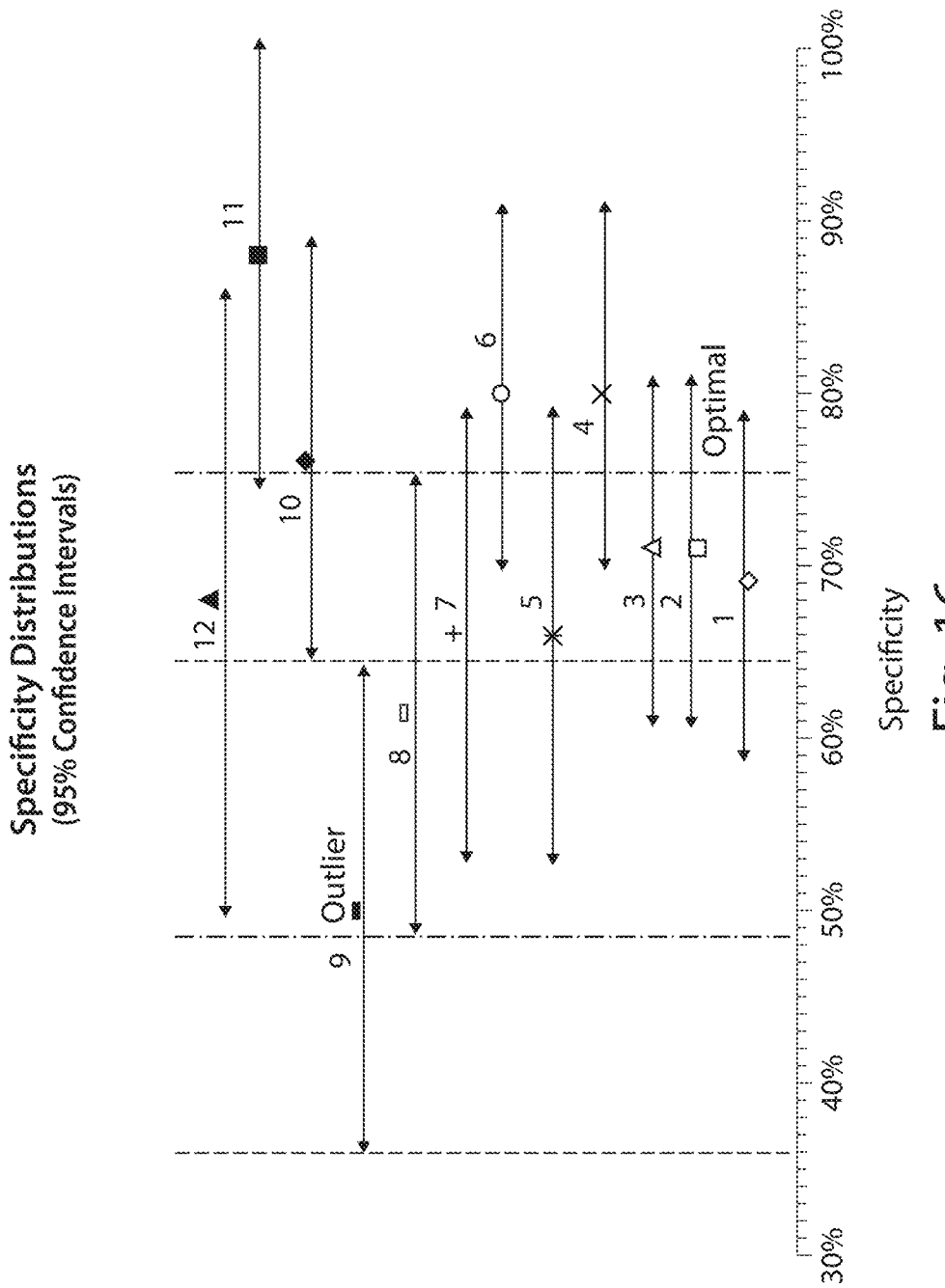
FIG. 16 is a plot of the specificity distributions for each validation test set as defined in Table 8 (i.e., the number above each double-headed arrow line corresponds to the validation test set with the same number in Table 8, the numbers are listed from 12 to 1 from top to bottom above each arrow).
Figure 17:
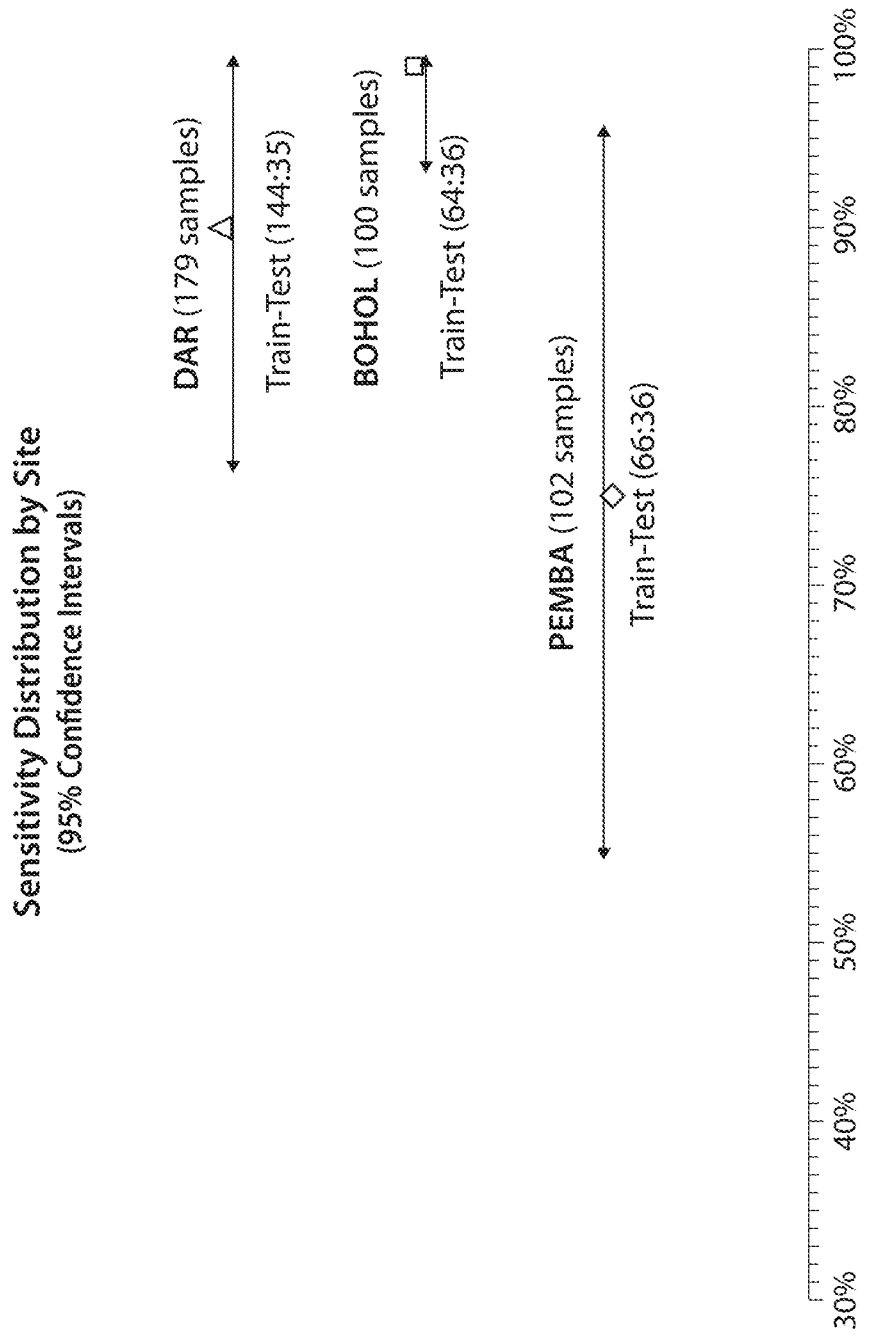
FIG. 17 is a plot of the sensitivity distribution for each cohort (Dar=D, Pemba=P, Bohol=B) using each cohort as the train/test set.
Figure 18:
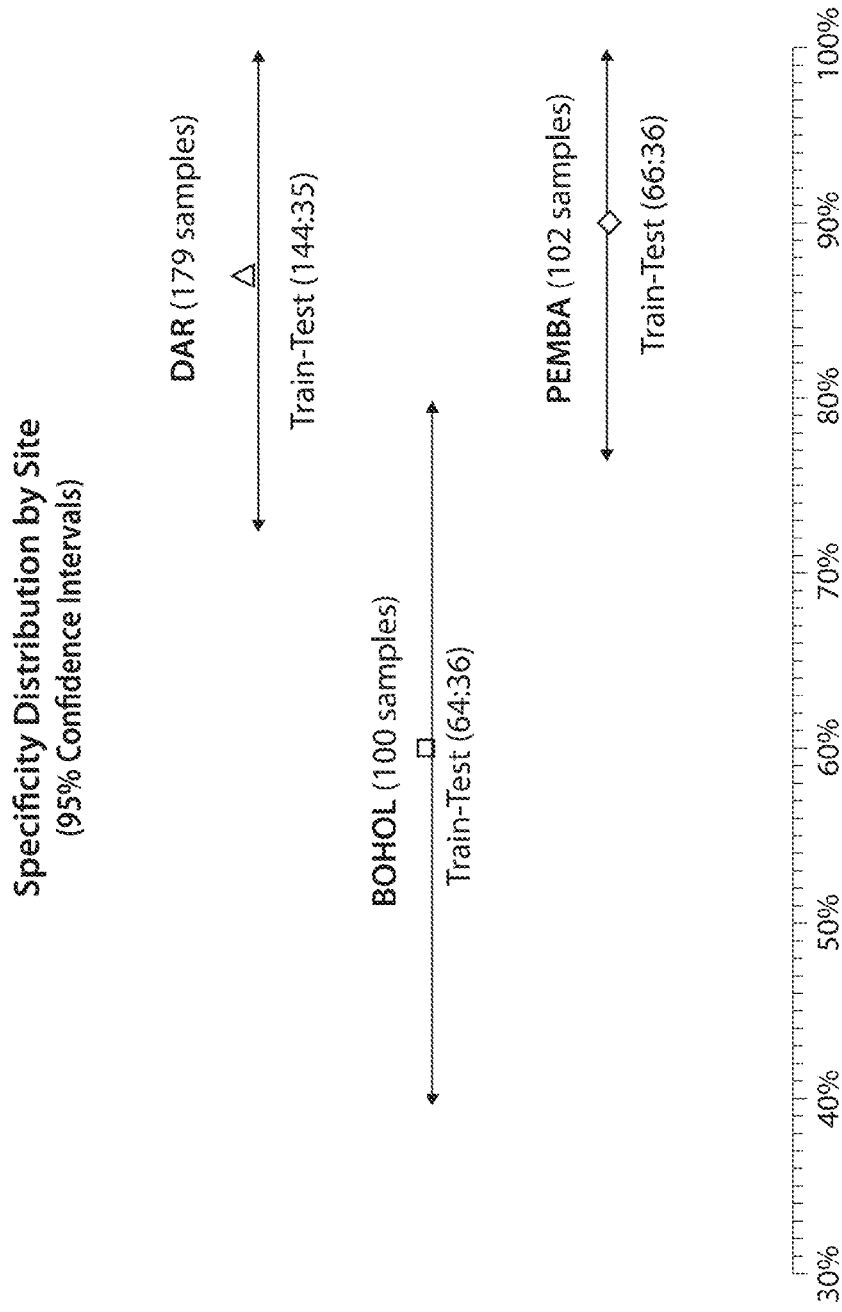
FIG. 18 is a plot of the specificity distribution for each cohort (Dar=D, Pemba=P, Bohol=B) using each cohort as the train/test set.

It was found that the sensitivity measurements with 95% confidence intervals for all twelve measurements overlapped and were consistent (FIG. 15). The specificity measurements with 95% confidence intervals for 11 of 12 measurements overlapped and were consistent (FIG. 16). The ninth measurement appeared to be an outlier. When data from the same site (DAR, BOHOL, or PEMBA) were used as the train/test set and the validation set (albeit split so that the samples in the train/test set and the validation set were different although all came from the same cohort), the sensitivity and specificity measurements with 95% confidence intervals for the three cohorts (Dar, Pemba and Bohol) overlapped and were consistent (FIG. 17 and FIG. 18).

Additional validations were performed using specific combinations of train/test sites and validation sites, as well as various combinations of the 5 biomarkers. The results of these further validations are shown in Table 8. Validation set #1 included IL-6, IL-8, IL-1RA, IL-18 and VEGF. Validation set #2 included IL-6, IL-8, IL-18 and VEGF. Validation set #3 included IL-6, IL-8 and VEGF. Validation set #6 included 19 cured TB cases after 6 months of DOTS (directly observed treatment, short-course) regimen. All other validation sets included IL-6, IL-8, IL-1RA, IL-18 and VEGF.

TABLE 8

Further validation using certain train/test sites and validation sites

| # | Train/Test Site | Validation Site | Validate #Cases | Validate #ill | Specificity | 95% CI (+/−) | Sensitivity | 95% CI (+/−) | % Correct | 95% CI Specificity Range | 95% CI Sensitivity Range |
|---|---|---|---|---|---|---|---|---|---|---|---|
| 1 | DAR, PEMBA, BOHOL | DAR, PEMBA, BOHOL | 74 | 75 | 0.69 | 0.10 | 0.77 | 0.10 | 73% | (59%-79%) | (67%-87%) |
| 2 | DAR, PEMBA, BOHOL | DAR, PEMBA, BOHOL | 74 | 75 | 0.71 | 0.10 | 0.87 | 0.08 | 79% | (61%-81%) | (79%-95%) |
| 3 | DAR, PEMBA, BOHOL | DAR, PEMBA, BOHOL | 74 | 75 | 0.71 | 0.10 | 0.82 | 0.09 | 77% | (61%-81%) | (73%-91%) |
| 4 | DAR | PEMBA | 51 | 51 | 0.80 | 0.11 | 0.75 | 0.12 | 78% | (69%-91%) | (63%-87%) |
| 5 | DAR | BOHOL | 50 | 50 | 0.66 | 0.13 | 0.80 | 0.11 | 73% | (53%-79%) | (69%-91%) |
| 6 | DAR | DAR Cured Cases | 0 | 19 | 0.84 | 0.16 | 0.00 | 0.00 | 84% | (68%-100%) | |
| 7 | BOHOL | DAR | 93 | 86 | 0.67 | 0.10 | 0.88 | 0.07 | 78% | (67%-77%) | (81%-95%) |
| 8 | BOHOL | PEMBA | 51 | 51 | 0.84 | 0.10 | 0.73 | 0.12 | 78% | (74%-94%) | (61%-85%) |
| 9 | PEMBA | DAR | 93 | 86 | 0.83 | 0.08 | 0.75 | 0.09 | 79% | (75%-91%) | (66%-84%) |
| 10 | PEMBA | BOHOL | 51 | 51 | 0.70 | 0.13 | 0.64 | 0.13 | 67% | (57%-83%) | (51%-77%) |

The results in Table 8 show that a 4 biomarker set excluding IL-1RA had improved sensitivity and specificity, indicating that IL-1RA may be excluded in some instances. The results in Table 8 also show that a 3 biomarker set excluding both IL-1RA and IL-18 did not perform better than the 4 biomarker set, indicating that IL-18 may be included in some instances.

Further, analysis the 5 biomarker set in 19 cured TB cases after 6 month of DOTS regimen (Table 8, #6) showed that 16/19 (84%) of the cured TB cases had a non-TB signature. These results indicate that these biomarkers may be used to determine treatment efficacy or treatment response, as well as the presence of TB infection.

Discussion

The results provided herein indicate that a blood-based host immune response signature exists for persistent coughers with active TB disease. The global analysis of all 381 samples from all 3 cohorts achieved 87% (95% CI: 79%-95%) sensitivity and 71% (95% CI: 61%-81%) specificity for a panel of 4 biomarkers (IL-6, IL-8, IL-18 and VEGF) within the pg/ml concentration range. The results from this global analysis point towards a high sensitivity (~90%) and relatively lower specificity (~70%) blood based diagnostic assay. Such an assay may be used, for example, as a "rule out" test, which is essential for TB control in endemic settings. Currently, ~40% sputum smear positive TB cases (who then infect others) remain undetected by prevailing sputum smear microscopy methods. A "rule out" test with high sensitivity may have a positive impact in TB control by identifying subjects that are unlikely to have TB. A significant advantage of a blood based assay using the 4 or 5 biomarker panel is that it doesn't require sputum, hence it needs minimal infrastructure. Furthermore, given that children have difficulty in producing sputum, this blood based assay may be especially useful for TB identification in children.

Additionally, the 5 biomarker panel (IL-6, IL-8, IL-18, IL-1RA and VEGF) correctly identified 84% (16 of 19) of DOTS treated TB patients as no longer exhibiting a TB biomarker pattern. The levels of the biomarkers in the blood of these 16 subjects were found to be reduced after treatment. The remaining 3 subjects had elevated levels compared to baseline, which may indicate potential treatment failure. Thus, the biomarker panel may also be useful for prognostic methods, such as determining treatment efficacy.

Without further elaboration, it is believed that one skilled in the art can, based on the above description, utilize the present invention to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

The indefinite articles "a" and "an," as used herein in the specification and in the claims, unless clearly indicated to the contrary, should be understood to mean "at least one."

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method comprising:
   (a) obtaining a blood sample from a human subject having one or more symptoms of tuberculosis (TB), and
   (b) detecting protein levels of three or more biomarkers in the blood sample by contacting the sample with antibodies or antigen-binding antibody fragments specific for each of the three or more biomarkers and detecting binding between each of the three or more biomarkers and its respective antibody or antigen-binding antibody fragment, wherein the biomarkers are selected from
      (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"); and/or
      (ii) a second group consisting of A2Macro, MMP-2, VCAM-1, IL-17, and SCF ("Group II biomarker").

2. The method of claim 1, wherein detecting protein levels comprises detecting protein levels of Group I biomarkers in the blood sample that are greater than pre-determined threshold levels, wherein the pre-determined threshold levels are levels of the Group I biomarkers in a blood sample from tuberculosis-negative subjects having a persistent cough.

3. The method of claim 1, wherein the three or more biomarkers are Group I biomarkers.

4. The method of claim 1, wherein the three or more biomarkers are Group II biomarkers.

5. The method of claim 1, wherein the three or more biomarkers are a combination of Group I biomarkers and Group II biomarkers.

6. The method of claim 1, wherein the three or more biomarkers are selected from the group consisting of IL-18, IL-1RA, IL-6, IL-8, and VEGF.

7. The method of claim 1, wherein the three or more biomarkers are selected from the group consisting of IL-18, IL-6, IL-8, and VEGF.

8. The method of claim 1, wherein the blood sample is a plasma or serum sample.

9. The method of claim 1, wherein the subject has a persistent cough.

10. The method of claim 1, wherein the subject is an adult.

11. The method of claim 1, wherein the protein levels are measured by an immuno-based assay.

12. The method of claim 1, wherein the three or more biomarkers are four biomarkers.

13. The method of claim 1, wherein the three or more biomarkers are five biomarkers.

14. A device comprising
    a sample inlet and
    binding partners for three or more biomarkers selected from the group consisting of
       (i) a first group consisting of AAT, Fibrinogen, Haptoglobin, C3, beta-2-macroglobulin, CRP, ICAM-1, TIMP-1, TNFR2, IL-18, IL-1RA, IL-6, IL-8, TNF-alpha, and VEGF ("Group I biomarker"), and/or
       (ii) a second group consisting of A2Macro, MMP-2, VCAM-1, IL-17, and SCF ("Group II biomarker"),
    wherein binding partners having the same biomarker binding specificity are grouped together on a substrate and groups are physically separated from each other on the substrate.

15. The device of claim 14, wherein the three or more biomarkers are Group I biomarkers.

16. The device of claim 14, wherein the three or more biomarkers are selected from the group consisting of IL-18, IL-1RA, IL-6, IL-8, and VEGF.

17. The device of claim 14, wherein the three or more biomarkers are IL-18, IL-6, IL-8, and VEGF.

18. The device of claim 14, wherein the three or more biomarkers are four biomarkers.

19. The device of claim 14, wherein the binding partners are antibodies or antigen-binding antibody fragments.

20. The device of claim 14, wherein the binding partners are antibodies.

21. The method of claim 1, wherein detecting protein levels comprises detecting protein levels of Group II biomarkers that are below pre-determined threshold levels, wherein the pre-determined threshold levels are levels of Group II biomarkers in a blood sample from tuberculosis-negative subjects having a persistent cough.

* * * * *